United States Patent
Kawata

(10) Patent No.: US 7,429,242 B2
(45) Date of Patent: Sep. 30, 2008

(54) ELECTRONIC ENDOSCOPE APPARATUS AND SIGNAL PROCESSING APPARATUS HAVING DETACHABLE OPTION SUBSTRATE

(75) Inventor: Susumu Kawata, Hachioji (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 10/694,212

(22) Filed: Oct. 27, 2003

(65) Prior Publication Data
US 2004/0085442 A1  May 6, 2004

(51) Int. Cl.
*A61B 1/04* (2006.01)

(52) U.S. Cl. .................... 600/109; 348/74; 348/75; 348/76

(58) Field of Classification Search ........... 600/109, 600/118; 348/74–76, 65
See application file for complete search history.

(56) References Cited

U.S. PATENT DOCUMENTS

| | | | |
|---|---|---|---|
| 4,719,516 A | | 1/1988 | Nagashima |
| 5,408,270 A | * | 4/1995 | Lim .................. 375/240.25 |
| 5,646,680 A | * | 7/1997 | Yajima ................... 348/74 |
| 5,689,612 A | * | 11/1997 | Abe ..................... 386/109 |
| 5,762,555 A | * | 6/1998 | Crump et al. ............. 463/41 |
| 5,929,901 A | * | 7/1999 | Adair et al. ............... 348/76 |
| 5,954,634 A | * | 9/1999 | Igarashi ................ 600/109 |
| 6,184,922 B1 | * | 2/2001 | Saito et al. ................ 348/65 |
| 6,219,091 B1 | * | 4/2001 | Yamanaka et al. .......... 348/65 |
| 6,449,006 B1 | * | 9/2002 | Shipp .................... 348/70 |
| 6,538,687 B1 | * | 3/2003 | Saito et al. ................ 348/65 |
| 6,690,410 B1 | * | 2/2004 | Mochida et al. ........... 348/76 |
| 6,858,004 B1 | * | 2/2005 | Ozawa et al. ............. 600/118 |
| 2001/0051762 A1 | * | 12/2001 | Murata et al. ............ 600/118 |
| 2003/0004398 A1 | * | 1/2003 | Takahashi ............... 600/109 |
| 2003/0025830 A1 | * | 2/2003 | Perry .................... 348/441 |
| 2004/0143157 A1 | * | 7/2004 | Doguchi et al. .......... 600/109 |

FOREIGN PATENT DOCUMENTS

| | | |
|---|---|---|
| JP | 7-298202 | 11/1995 |
| JP | 2000-210251 | 8/2000 |
| JP | 2000-354240 | 12/2000 |
| JP | 2001-70241 | 3/2001 |
| JP | 2001-76124 | 3/2001 |
| JP | 2001-78174 | 3/2001 |

* cited by examiner

*Primary Examiner*—John P Leubecker
(74) *Attorney, Agent, or Firm*—Scully, Scott, Murphy & Presser, P.C.

(57) ABSTRACT

An electronic endoscope including a CCD is detachably connected to a video processor. In the video processor, an output signal from the CCD is A/D converted, white balance is adjusted, an NTSC video signal from a post-process circuit is subjected to processing for generating a basic video signal to be outputted to a monitor, and an option substrate having a connector detachable to a connector for outputting a signal after AGC processing is attached thereto. Thus, user's desired function such as output to the monitor by emphasis processing can easily be realized by attaching the option substrate or the like.

26 Claims, 18 Drawing Sheets

FIG.9A

```
Clock                    VTR Setup
  Type YYYY/MM/DD          Type RS232C
  Date  2001/07/02
  Time  15:00:00           Release Time
                             05/1/2
Monitor Setup
  TypeA                  Enhance Setup
  TypeB                    ON/OFF Printer Setup            Digital Out Setup
  TypeA                    ON/OFF
  TypeB
```

FIG.9B

```
Clock                    VTR Setup
  Type YYYY/MM/DD          Type RS232C
  Date  2001/07/02
  Time  15:00:00           Release Time
                             05/1/2
Monitor Setup
  TypeA                  Enhance Setup
  TypeB                    ON/OFF Printer Setup            Digital Out Setup
  TypeA                    ON/OFF
  TypeB
```

FIG.9C

```
Clock                    VTR Setup
  Type YYYY/MM/DD          Type RS232C
  Date  2001/07/02
  Time  15:00:00           Release Time
                             05/1/2
Monitor Setup
  TypeA                  ┌----------------┐
  TypeB                  └----------------┘

Printer Setup            ┌----------------┐
  TypeA                  └----------------┘
  TypeB
```

No.123456
OLY
M
2001. 07. 02

HDTV

No.123456
OLY
M
2001. 07. 02

NTSC

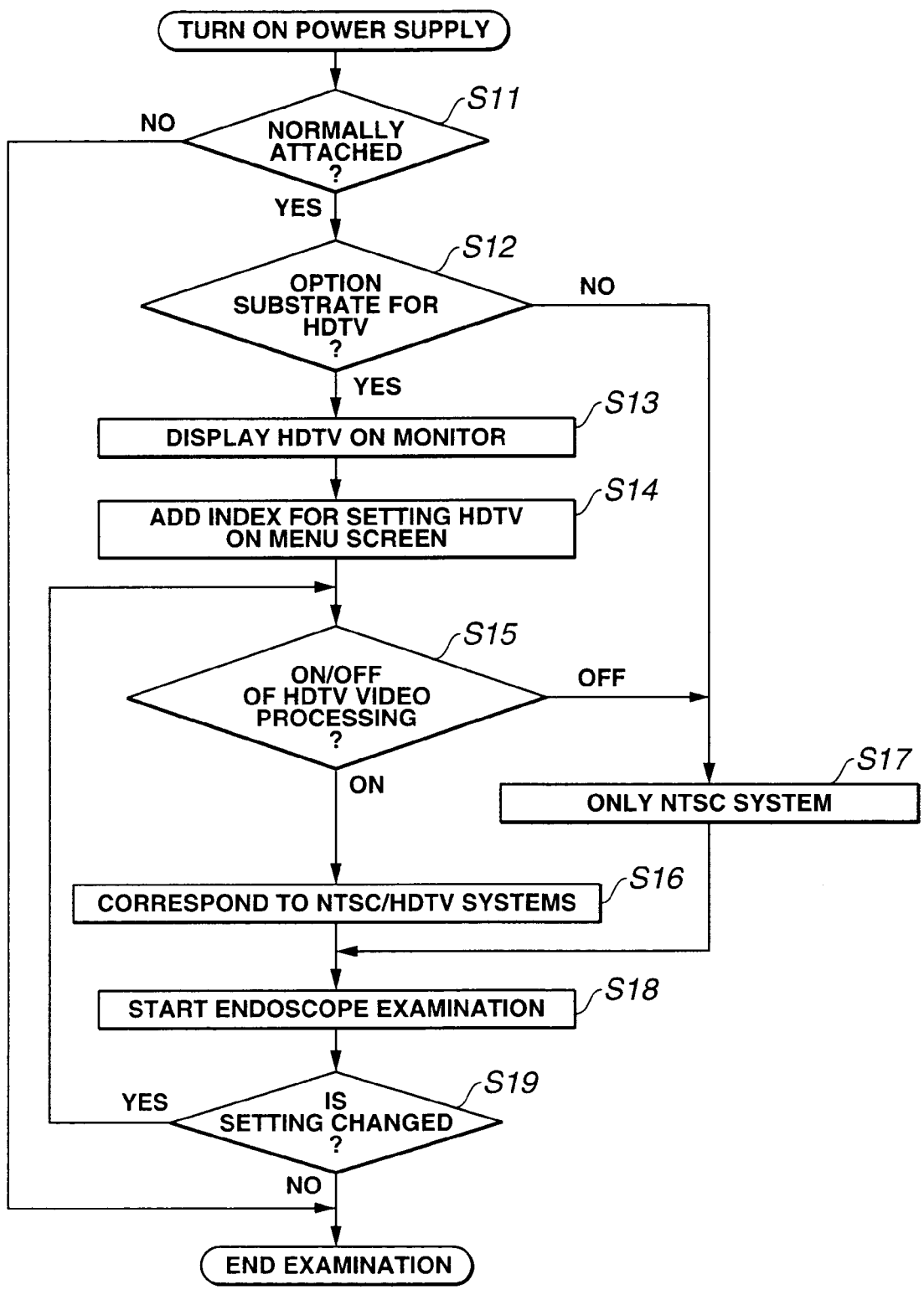

ELECTRONIC ENDOSCOPE APPARATUS AND SIGNAL PROCESSING APPARATUS HAVING DETACHABLE OPTION SUBSTRATE

CROSS REFERENCE OF RELATED APPLICATIONS

The present application is based on (1) Japanese Patent Application No. 2001-218606 filed on Jul. 18, 2001 as claims of priority. The disclosure in the above application (1) is referred to the specification of the present application, claims, and drawings.

TECHNICAL FIELD

The present invention relates to an electronic endoscope apparatus and a signal processing apparatus for performing signal processing for an electronic endoscope or the like.

BACKGROUND ART

In recent years, endoscopes have widely been used for examination in medical and industrial fields. An electronic endoscope having an image pick-up device is recently used.

A video processor is used for the electronic endoscope as a signal processing apparatus for performing signal processing of the image signal which is picked up by the image pick-up device.

FIG. 24 shows a conventional electronic endoscope apparatus 61. The electronic endoscope apparatus 61 comprises an electronic endoscope 62, a video processor 63 connected to the electronic endoscope 62, and a monitor 64 for displaying a video signal outputted from the video processor 63.

The video processor 63 comprises a floating circuit 70 which is further insulated from a secondary circuit at a portion connected to the image pick-up device incorporated in the electronic endoscope 62.

The floating circuit 70 comprises a drive circuit 71 for driving the image pick-up device, a pre-process circuit 72 for amplifying the image signal which is photoelectrically converted by the image pick-up device by applying a drive signal from the drive circuit 71, and an A/D converting circuit 73 for converting an output signal as an analog signal from the pre-process circuit 72 into a digital signal.

The digital signal converted by the A/D converting circuit 73 is inputted to a white balance circuit (abbreviated to a W/B) 74 forming a part of a secondary circuit 83 via an insulating circuit such as a photocoupler (not shown). The secondary circuit 83 corresponds to a part other than the floating circuit 70 in the video processor 63.

After adjusting the white balance by the white balance circuit 74, the signal is inputted to an automatic gain control circuit (AGC circuit) 75. An amplitude of the signal is amplified to a predetermined level and thereafter the signal is inputted to a gamma circuit (abbreviated to a γ circuit) 76. After γ correction, the signal is inputted and is temporarily written to a field memory 77.

The signal written to the field memory 77 is read at a predetermined timing, and is converted into the analog signal by a D/A converting circuit 78. Then, the signal is inputted to a post process circuit 79, is subjected to processing for converting the signal into the video signal, becomes the video signal, and is outputted to the monitor 64 from an output terminal.

The video processor 63 comprises a PLL circuit 81 for generating a signal synchronous with a reference clock to generate a reference signal, and a synchronous signal generating circuit (abbreviated to an SSG) 82 for generating horizontal and vertical synchronous signals synchronously with the PLL circuit 81. An output signal from the synchronous signal generating circuit 82 is applied to a circuit necessary for the synchronous signal, thereby performing processing synchronously with the synchronous signal.

The secondary circuit has a large-scaled FPGA (field programmable gate array) circuit formed by recent device technologies. In the circuit scale forming the conventional function, a device occupying area on a substrate is reduced. The circuit scale is formed by substantially single substrate.

However, in the case of adding a new function and another-TV-system signal processing circuit, the circuit scale is increased and it cannot be formed by the single substrate. Then, it is considered that the number of substrates including the entire functions is plural in the first step of the development. However, this is not advantageous in views of development costs and products.

Facilities using the electronic endoscope apparatus are varied and functions required for the facilities are also varied. One user needs the emphasis of pathology which is performed by visualizing invisible information using an image processing function, a support diagnosis function, high resolution, high picture quality, and the like. Another user needs only a necessary observation function and the like with a low price. It is desired that the electronic endoscope apparatus corresponding to wide users are to be sold.

The present invention is devised in consideration of the above circumstances. It is an object of the present invention to provide an electronic endoscope apparatus and a signal processing apparatus which can correspond to the requests of wide users with low costs.

BRIEF SUMMARY OF THE INVENTION

An electronic endoscope apparatus of the first invention for outputting a video signal, to which an endoscope is detachably connected, comprises:

an image pick-up device for photoelectrically converting a subject image and outputting an image signal;

A/D converting means for converting an output signal of the image pick-up device into a digital signal;

first signal processing means for performing processing of the signal converted by the A/D converting means corresponding to a first output format and outputting the video signal from a video signal output terminal; and second signal processing means provided for a substrate detachably connected to a connector for outputting the signal converted by the A/D converting means, for performing imaging processing of the converted signal and outputting the video signal corresponding to a second output format.

According to the first invention, the first signal processing means includes, for example, a field memory 19, a D/A converting circuit 20, and a post-process circuit 21, which are shown in FIG. 1. The second signal processing means includes a field memory 27, a D/A converting circuit 28, and a post-process circuit 29, which are shown in FIG. 1.

An electronic endoscope apparatus of the second invention for outputting a video signal, to which an endoscope is detachably connected, comprises:

an image pick-up device for photoelectrically converting a subject image and outputting an image signal;

A/D converting means for converting an output signal of the image pick-up device into a digital signal;

first signal processing means for performing first signal processing of the converted signal;

second signal processing means for performing processing of the image signal processed by the first signal processing means corresponding to a first output format;

first output means for outputting the image signal processing by the second signal processing means; and a substrate comprising third signal processing means detachably connected to a connector for outputting the image signal processed by the first signal processing means, for performing processing of the image signal corresponding to a second output format different from the first format, and second output means for outputting the image signal processed by the third signal processing means.

According to the second invention, the first signal processing means includes, for example, a W/B circuit 15, an AGC circuit 16, a γ circuit 18, and the like, which are shown in FIG. 1. The second signal processing means includes the field memory 19, the D/A converting circuit 20, and the post-process circuit 21. The first output means includes a video output terminal Vo on a video processor 4 side. The third signal processing means includes an emphasis processing circuit 25, a correction processing circuit 26, the field memory 27, the D/A converting circuit 28, the post-process circuit 29, and the like. The second output means includes a video output terminal Vo on an option substrate 7 side.

A signal processing apparatus of the third invention comprises:

an image pick-up device for photoelectrically converting a subject image and outputting an image signal;

A/D converting means for converting an output signal of the image pick-up device into a digital signal;

first signal processing means for performing processing of the signal converted by the A/D converting means corresponding to a first output format and outputting a video signal from a video signal output terminal; and second signal processing means provided for a substrate detachably connected to a connector for outputting the signal converted by the A/D converting means, the second signal processing means for performing imaging processing of the converted signal and outputting the video signal corresponding to a second output format.

According to the third invention, the first and second signal processing means includes the same portions as those according to the first invention. The first signal processing means includes, for example, the field memory 19, the D/A converting circuit 20, and the post-process circuit 21, which are shown in FIG. 1. The second signal processing means includes the field memory 27, the D/A converting circuit 28, and the post-process circuit 29.

A signal processing apparatus of the fourth invention comprises:

an image pick-up device for photoelectrically converting a subject image and outputting an image signal;

A/D converting means for converting an output signal of the image pick-up device into a digital signal;

first signal processing means for performing first signal processing of the converted signal;

second signal processing means for performing processing of the image signal processed by the first signal processing means corresponding to a first output format;

first output means for outputting the image signal processing by the second signal processing means; and a substrate comprising third signal processing means detachably connected to a connector for outputting the image signal processed by the first signal processing means, for performing processing of the image signal corresponding to a second output format different from the first format, and second output means for outputting the image signal processed by the third signal processing means.

According to the fourth invention, the first to third signal processing means and the first and second output means include the same portions as those according to the second invention, respectively. The first signal processing means includes, for example, the W/B circuit 15, the AGC circuit 16, the γ circuit 18, and the like, which are shown in FIG. 1. The second signal processing means includes the field memory 19, the D/A converting circuit 20, and the post-process circuit 21. The first output means includes the video output terminal Vo on the video processor 4 side. The third signal processing means includes the emphasis processing circuit 25, the correction processing circuit 26, the field memory 27, the D/A converting circuit 28, the post-process circuit 29, and the like. The second output means includes the video output terminal Vo on the option substrate 7 side.

With the above-mentioned structure of the electronic endoscope apparatus or signal processing, the substrate is not attached or the substrate is attached, a function can easily be selected corresponding to user's desired function for generating the basic video signal or user's desired function. Accordingly, the electronic endoscope apparatus or signal processing apparatus can correspond to user's wide requests with low costs.

BRIEF DESCRIPTION OF THE DRAWINGS

FIG. 9A is a diagram showing one display example of a menu screen when the option substrate is not connected.

FIG. 9B is a diagram showing a display example of the menu screen when the option substrate is connected.

FIG. 9C is a diagram showing another display example of the menu screen when the option substrate is not connected.

FIG. 19 is a flowchart for explaining the operation according to the fifth embodiment.

BEST MODE FOR CARRYING OUT THE INVENTION

Herein below, embodiments of the present invention will be described with reference to the drawings.

First Embodiment

Figure 1:
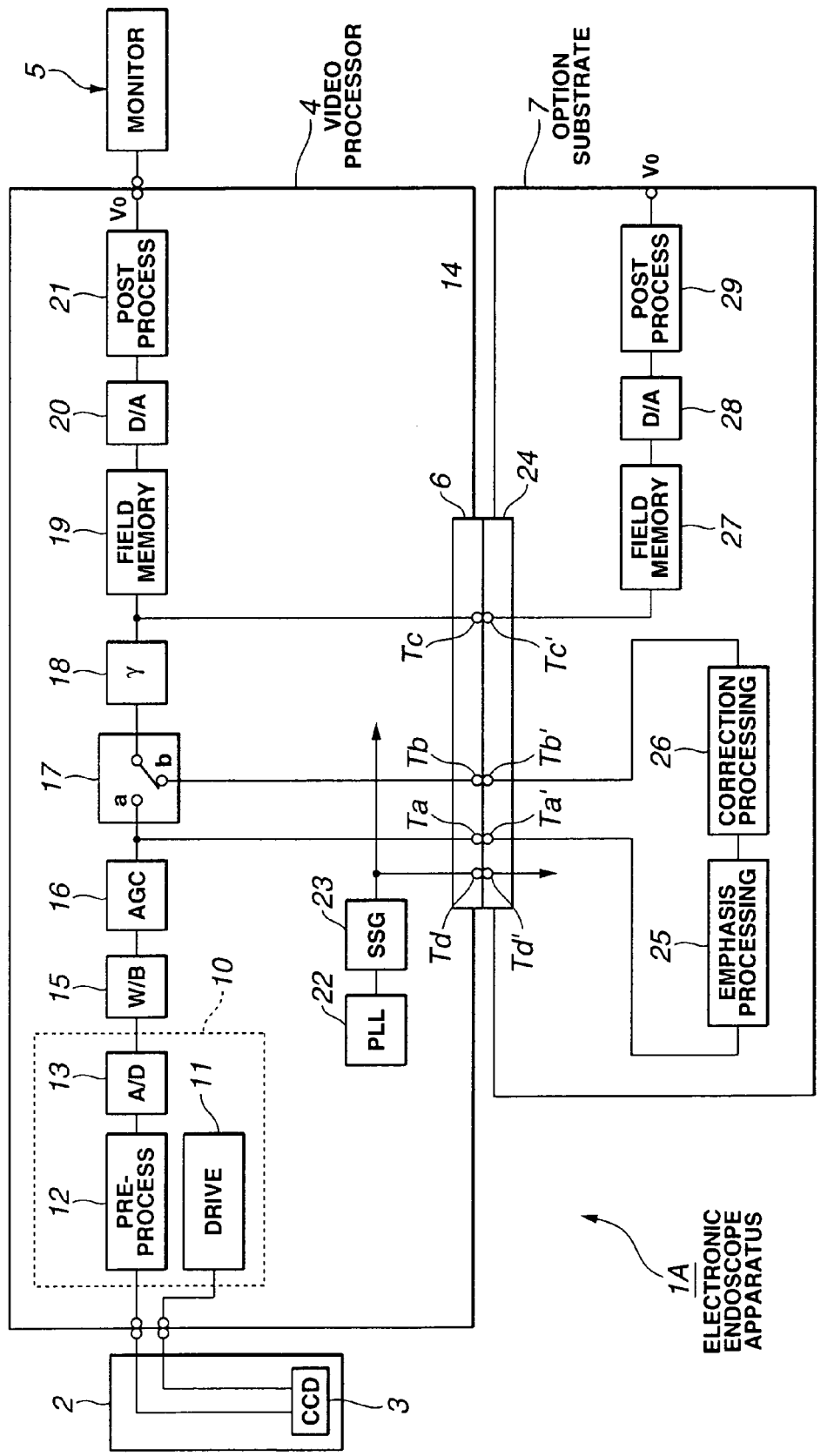
FIG. 1 is a block diagram showing the structure of an electronic endoscope apparatus according to a first embodiment of the present invention.
Figure 2:
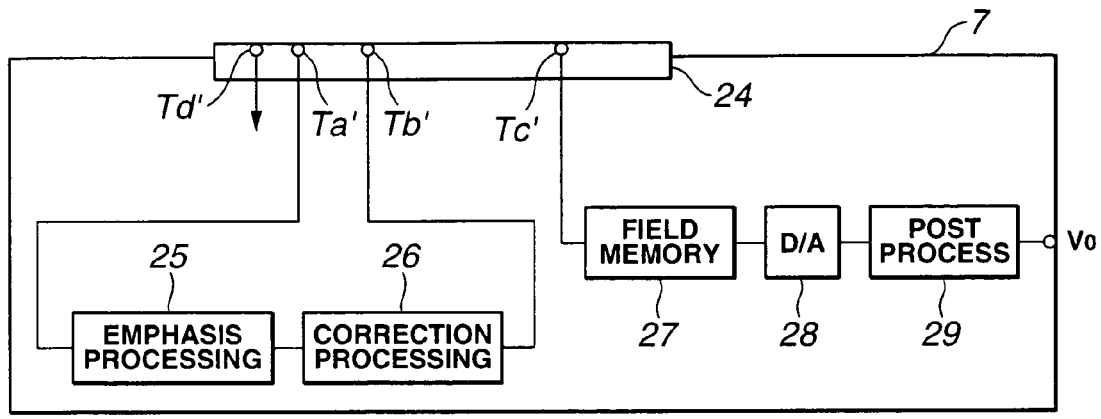
FIG. 2 is a block diagram showing the circuitry structure of a first option substrate.
Figure 3:
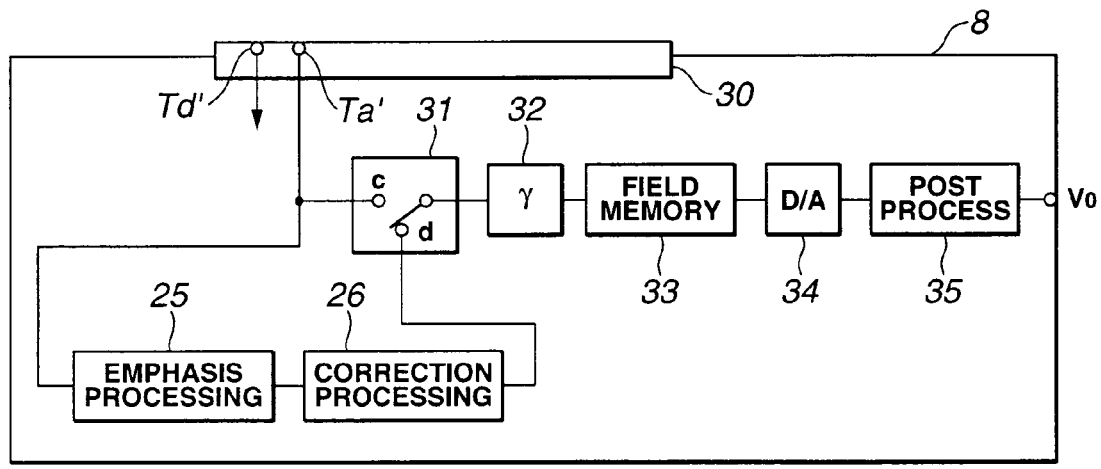
FIG. 3 is a block diagram showing the circuitry structure of a second option substrate.
Figure 4:
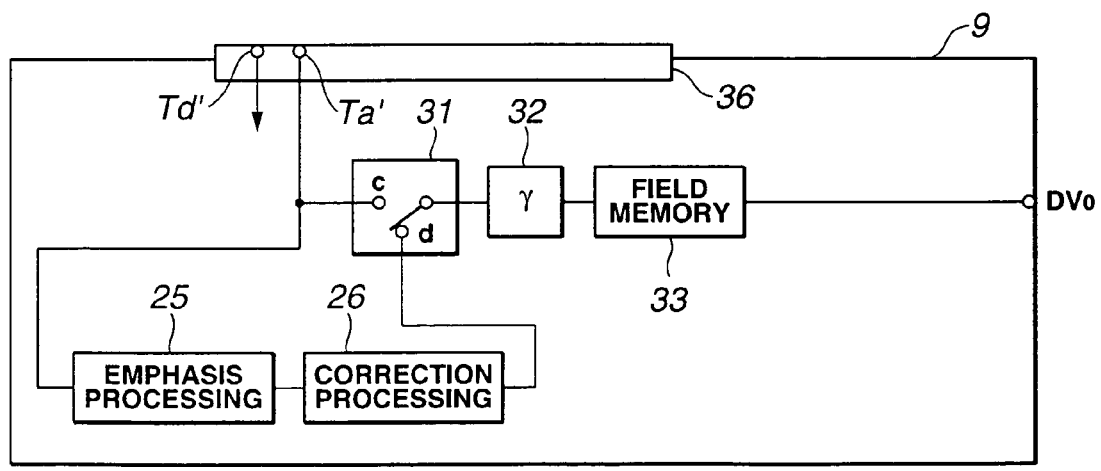
FIG. 4 is a block diagram showing the circuitry structure of a third option substrate.

FIGS. 1 to 4 relate to a first embodiment of the present invention, FIG. 1 shows the entire structure of an electronic endoscope apparatus according to the first embodiment, and FIGS. 2 to 4 show structure examples of first to third option substrates which can be attached to a signal processing apparatus.

Referring to FIG. 1, an electronic endoscope apparatus (hereinafter, abbreviated to an endoscope apparatus) 1A comprises an electronic endoscope 2, a video processor 4 for performing signal processing for a CCD 3 as an image pick-up device incorporated in the electronic endoscope 2 which is detachably attached thereto, a monitor 5 as image display means for displaying an endoscope image picked up by the CCD 3 by inputting a video signal outputted from the video processor 4, and a light source device (not shown) for supplying illumination light to the electronic endoscope 2. The video processor 4 comprises a floating circuit 10 and a secondary circuit 14 which is insulated from the floating circuit 10.

According to the first embodiment, the video processor 4 comprises a connector 6. The function of the video processor 4 can be expanded by attaching any of first to third option substrates 7 to 9 having various functions shown in FIGS. 2 to 4 to the connector 6. FIG. 1 shows a state in which the first option substrate 7 shown in FIG. 2 is attached to the connector 6.

According to the first embodiment, the video processor 4 comprises the floating circuit 10 which is electrically insulated from the secondary circuit 14, at a connection portion of the CCD 3. The floating circuit 10 comprises a drive circuit 11 for driving the CCD 3, a pre-process circuit 12 for performing pre-processing such as CDS processing for extracting a signal component from an image pick-up signal photoelectrically converted by the CCD 3 by applying a drive signal from the drive circuit 11, and an A/D converting circuit 13 for converting an analog signal of an output signal from the pre-process circuit 12 into a digital signal.

The digital signal converted by the A/D converting circuit 13 is inputted to a white balance circuit (abbreviated to a W/B circuit) 15 forming a part of the secondary circuit 14 via an insulating circuit such as a photocoupler (not shown). The circuits other than the floating circuit 10 shown by a broken line in FIG. 1 correspond to the secondary circuit 14. Therefore, the option substrate 7 attached to the connector 6 forms the secondary circuit and is electrically insulated from the floating circuit 10.

After adjusting the white balance by the white balance circuit 15, the signal is inputted to an automatic gain control circuit (AGC circuit) 16. An amplitude of the signal is amplified to a predetermined level and thereafter the signal is inputted to one contact a of a selector 17 and is applied to a terminal Ta of the connector 6. Another contact b of the selector 17 is connected to a terminal Tb of the connector 6.

An output signal of the selector 17 is inputted to a gamma circuit (abbreviated to a γ circuit) 18. After γ correction, the signal is inputted and is temporarily written to a field memory 19. Further, the signal is applied to a terminal Tc of the connector 6.

The signal written to the field memory 19 is read at a predetermined timing, and is converted into the analog signal by a D/A converting circuit 20. Then, the signal is inputted to a post-process circuit 21, is subjected to processing for converting the signal into the video signal, becomes the video signal, herein, an NTSC video signal, and is outputted to a monitor 5 from a video output terminal Vo as output means.

The video processor 4 comprises a PLL circuit 22 for generating a signal synchronous with a reference clock to generate a reference signal, and a synchronous signal generating circuit (abbreviated to an SSG) 23 for generating horizontal and vertical synchronous signals synchronously with the PLL circuit 22. An output signal from the synchronous signal generating circuit 23 is applied to a circuit necessary for the synchronous signal, thereby performing processing synchronously with the synchronous signal. The synchronous signal is also applied to a terminal Td of the connector 6.

According to the first embodiment, the video processor 4 has fundamental functions necessary for generating a predetermined video signal when the option substrate is not attached to the connector 6.

The first option substrate 7 having a connector 24 which can be attached to the connector 6 comprises an emphasis processing circuit 25 for performing emphasis processing of a contour, color, and the like at a terminal Ta' conductive to the terminal Ta connected to the output terminal of the AGC circuit 16. The emphasis processed signal further passes through a correction processing circuit 26 for performing correction processing and passes through the terminal Tb conductive to the terminal Tb' from the terminal Tb', and is inputted to the contact b of the selector 17. Therefore, the selector 17 selects the contact b and a video signal of the emphasis processed signal of an original image is outputted to the monitor 5 from the video output terminal Vo. When the selector 17 selects the contact a, the video signal of the same image as that of the conventional art is outputted to the monitor 5 from the video output terminal Vo.

A field memory 27 is connected to a terminal Tc' conductive to the terminal Tc. A signal which is temporarily stored in the field memory 27 is returned to the analog signal by a D/A converting circuit 28. Thereafter, the signal passes through a post-process circuit 29 and is converted into a predetermined format signal such as an NTSC video signal. Then, the signal is outputted to an external monitor or the like from the video output terminal Vo as the output means.

A synchronous signal is applied to the emphasis processing circuit 25 or the like of the first option substrate 7 from a terminal Td' conductive to a terminal Td.

As mentioned above, the option substrate 7 is attached to the connector 6 of the video processor 4 and the connector 17 is switched to the contact b. Then, the image signal passes through an emphasis processing function (25, 26). The same emphasis processed video signal can be outputted from a video processing system (19, 20, 21) on the video processor 4 side and from a video processing system (27, 28, 29) on the option substrate 7 side. When the connector 17 is switched to the contact a, the image signal does not pass through the emphasis processing function (25, 26). It is possible to output the same signal which is not subjected to the emphasis processing from the video processing system (19, 20, 21) on the video processor 4 side and from the video processing system (27, 28, 29) on the option substrate 7 side.

The second option substrate 8 shown in FIG. 3 has a connector 30 which is attached to the connector 6. Similarly to the case of the first option substrate 7 shown in FIG. 2, the emphasis processing circuit 25 is connected to the terminal Ta' and an output signal thereof is inputted to the correction processing circuit 26.

An input signal of the original image to the emphasis processing circuit 25 and an output signal of the image which passes through the emphasis processing circuit 25 and the correction processing circuit 26 to be subjected to the emphasis processing pass through contacts c and d of a selector 31 and are inputted to a γ circuit 32, are subjected to the γ correction, thereafter, are temporarily stored in a field memory 33, are read out, are returned to the analog signal via a D/A converting circuit 34, pass through a post-process circuit 35, and are outputted as the video signal to the external monitor or the like from the video output terminal Vo. When the contact c of the selector 31 is selected, the same signal as that of the main body video processor 4 is outputted from the video output terminal Vo. When contact d is selected, another image signal which is subjected to the emphasis processing is outputted from the video output terminal Vo.

The third option substrate 9 shown in FIG. 4 has a connector 36 which is attached to the connector 6. On the second option substrate 8 shown in FIG. 3, the third option substrate 9 outputs a digital video output signal from the filed memory 33 from a digital video output terminal DVo. When the contact c of the selector 31 is selected, the same image data as that of the main body video processor 4 is digitally outputted from the video output terminal DVo. When the contact d is selected, another image data which is subjected to the emphasis processing is digitally outputted from the video output terminal DVo.

As will be understood with reference to FIG. 1, the option substrate 7 or the like is connected to the secondary circuit 14 in the video processor 4, thereby individually having a predetermined function.

According to the first embodiment, the CCD 3 is subjected to basic processing and the video processor 4 comprises a single FPGA substrate (hereinafter, abbreviated to a basic substrate) to have a function for generating a standard video signal. Various option substrates 7 to 9 can be attached to the connector 6 provided on the basic substrate and the user's desired function can easily be expanded.

As compared with the case where the video processors having varied functions are individually provided, video processors having varied functions which are formed only by selectively attaching the expansion substrate are commonly used to the same basic substrate. It is possible to correspond to wide users with low costs.

As the operation according to the first embodiment, the user who requires a function for basically displaying a video image can use the video processor 4 which does not need the option substrate. Thus, the video processor 4 can be used for endoscope examination with low costs.

On the other hand, in the case of the user who desires an additional function as well as the basic function, the user buys an option substrate corresponding to the additional function and attaches the option substrate. Thus the user can perform the endoscope examination by using the video processor having the additional function. That is, the signal processing apparatus corresponding to the wide users can be realized by selectively attaching the option substrate. In this case, the signal processing can be realized only by selectively attaching the option substrate with low costs.

The user first buys the option substrate with the basic function and thereafter buys the option substrate according to the necessity. Thus, the user can select the expansion function with low costs.

As mentioned above, according to the first embodiment, it is possible to provide a signal processing apparatus and an electronic endoscope apparatus corresponding to user's wide requests with low costs.

Second Embodiment

Figure 5:
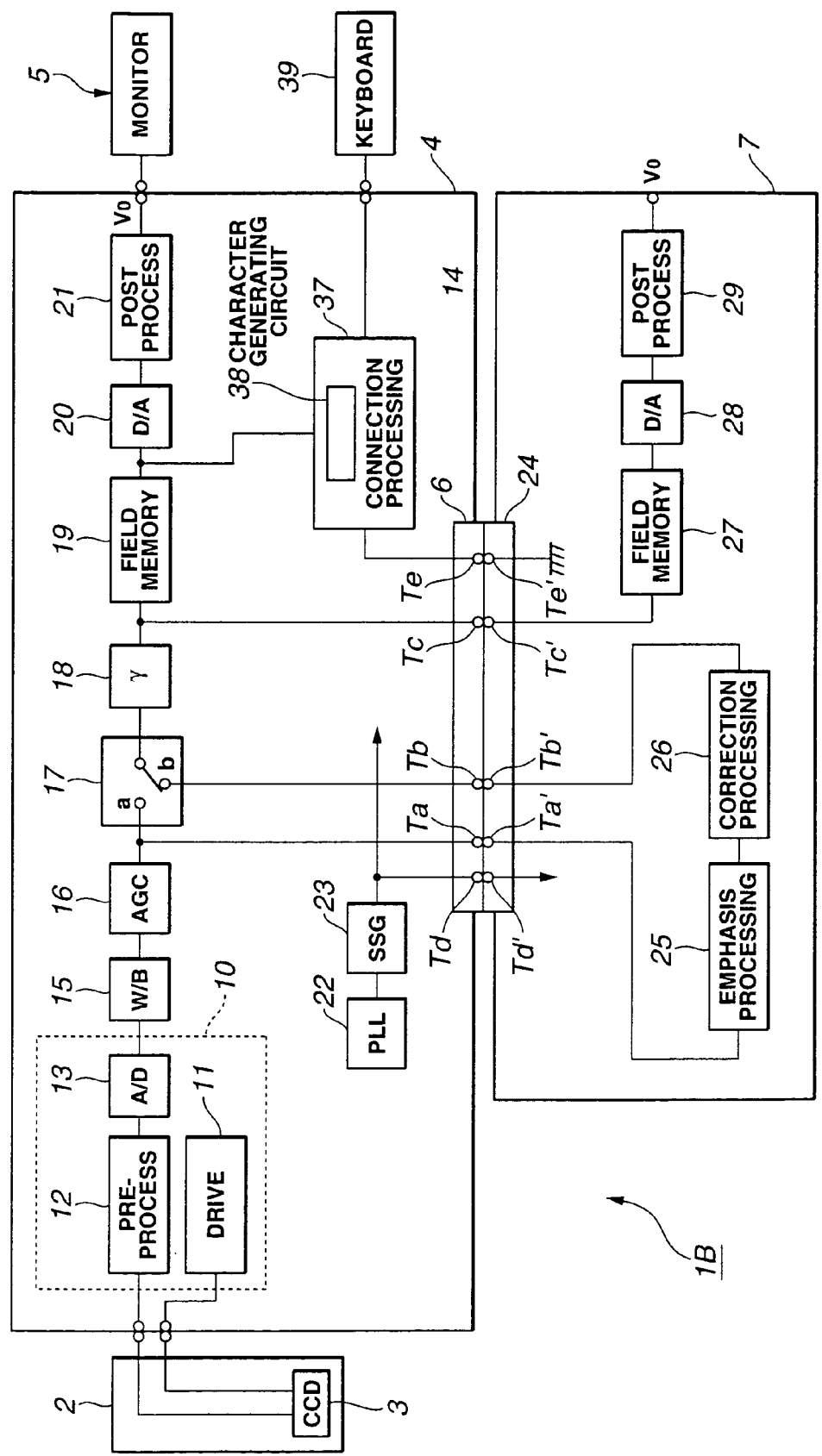
FIG. 5 is a block diagram showing the structure of an electronic endoscope apparatus according to a second embodiment of the present invention.

Next, a second embodiment of the present invention will be described with reference to FIGS. 5 to 10. FIG. 5 shows an endoscope apparatus 1B according to the second embodiment. In the endoscope apparatus 1B, the video processor 4 in the endoscope apparatus 1A in FIG. 1 further comprises a connection processing circuit 37 as connection detecting means for performing processing for detecting the connection of the substrate.

The connection processing circuit 37 is connected to a terminal Te of the connector 6. It is determined whether or not the option substrate is attached to the connector 6 by potential of the terminal Te. Further, it is detected (identified) which option substrate is attached.

The connection processing circuit 37 incorporates a character generating circuit 38 as character information generating means for generating character information (and character information on a menu screen) corresponding to a result of the connection detection, superimposes the generated character information to the output data of the field memory 19, and outputs the data to the D/A converting circuit 20 connected to the later step. Incidentally, in the case of the attaching the option substrate, the on/off operation of the expanding function is set by displaying the menu from such as a key board 39.

A terminal Te' conductive to the terminal Te, provided for, for example, the connector 24 of the first option substrate 7 attached to the connector 6 of the video processor 4, is connected to the ground of the secondary circuit 14.

Figure 6:
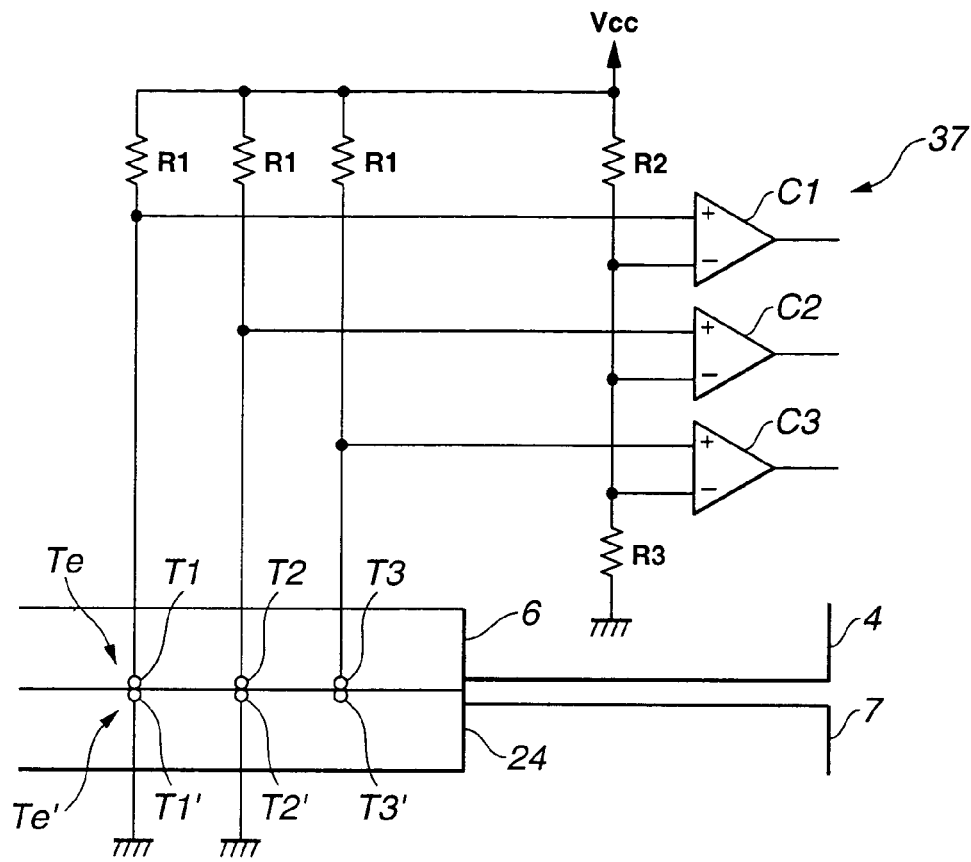
FIG. 6 is a circuitry diagram showing one example of the structure of a connection processing circuit.

FIG. 6 shows the circuitry structure for detecting the connection of the substrate. The terminals Te and Te' comprise, for example, three terminals T1 to T3 and T1' to T3', respectively.

The terminals T1 to T3 are connected to a power supply terminal Vcc (referred to a Vcc as a voltage for purpose of a brief description) by a resistor R1, and are connected to non-inversion input terminals of comparators C1 to C3 for determining the potential. A reference potential, for example, the power supply terminal voltage Vcc in this case, is divided by resistors R2 and R3 to obtain voltage values, and the voltage values are applied to the inversion input terminal. Double-value comparison output signals of the comparators C1 to C3 are results for detecting the substrate connection and for substrate function.

On the other hand, terminals T1' of the first to third option substrates 7 to 9 are connected to the ground. Therefore, when the output signal of the comparator C1 is H, the signal becomes a non-connection detecting signal of the substrate. When the output signal of the comparator C1 is L, the signal becomes a detection signal of the substrate connection.

The terminals T2' and T3' are connected to the ground in accordance with the type of substrate and are not connected to the ground. The connection of the first to third option substrates 7 to 9 may be detected by combining the outputs of the comparators C2 and C3.

The functions of the connected option substrates may be detected by using the outputs of the comparators C1 to C3. For example, it may be detected whether or not the imaging processing function is provided by the output of the comparator C2. Further, it may be detected whether the digital output or the analog output by using the output of the comparator C3.

In the case of connecting the substrate 7, for example, the terminal T2' is connected to the ground and the terminal T3' is not connected to the ground. In the case of connecting the substrate 9, the terminal T2' is connected to the ground and the ground T3' is connected to the ground.

In this case, when the output signal of the comparator C2 is L, the signal becomes the signal for detecting the connection of the substrate with the image processing function. When the output signal of the comparator C2 is H, the signal becomes the signal for detecting the connection of the substrate without the imaging processing function.

When the output signal of the comparator C3 is L, the signal becomes the signal for detecting the connection of the substrate with a digital output function. When the output signal of the comparator C3 is H, the signal becomes the signal for detecting the connection of the substrate with an analog output function.

In addition, a terminal for detecting whether or not the option substrate for HDTV, which will be described later, is attached may be provided.

Figure 8A:
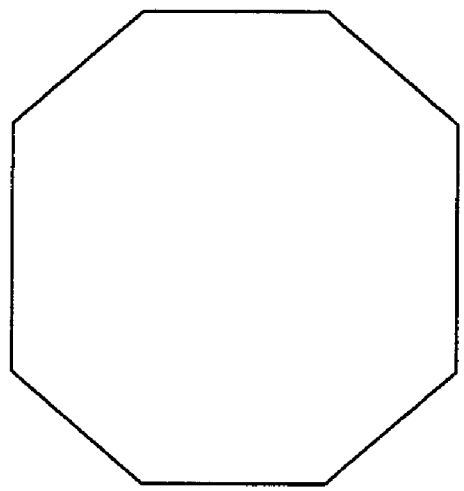
FIG. 8A is a diagram showing a display example of a monitor when the option substrate is not connected.
Figure 8B:
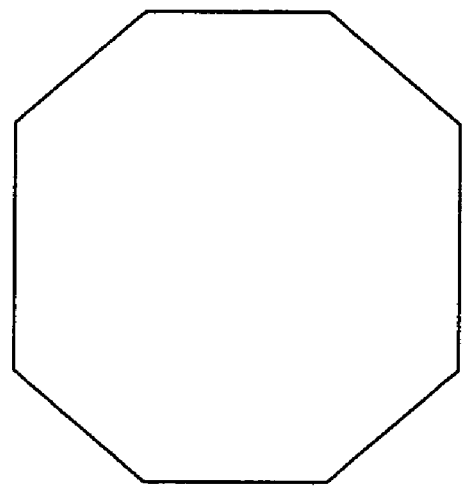
FIG. 8B is a diagram showing a display example of the monitor when the option substrate is connected.

FIG. 8A shows a display example of the monitor 5 when the option substrate is not connected, and FIG. 8B shows a display example of the monitor 5 when the option substrate is connected. Indication "option" is displayed as the result for detecting the connection of the option substrate. Although only the result for detecting the connection of the substrate using the comparator C1 is displayed as shown in FIGS. 8A and 8B, a result for detecting another substrate function may be displayed.

Figure 7:
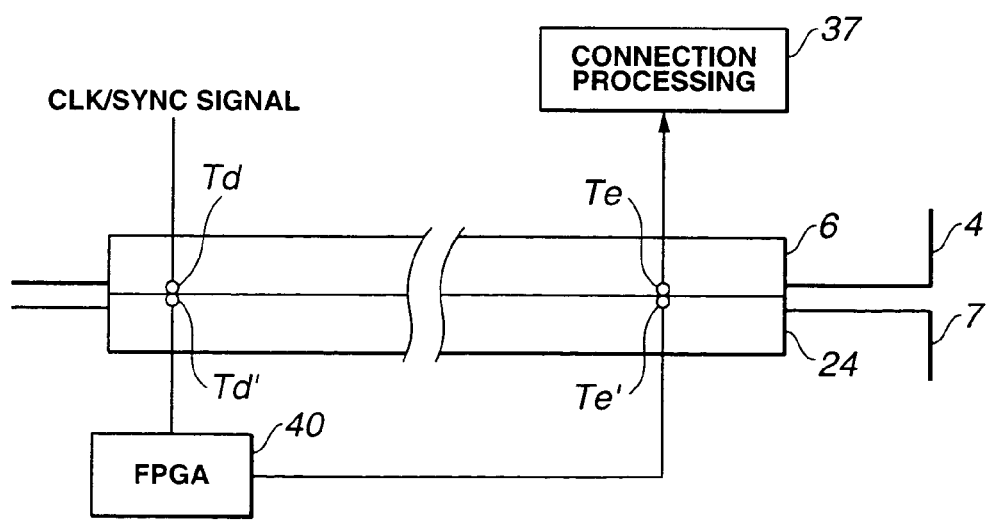
FIG. 7 is a circuitry diagram showing another example of the structure of the connection processing circuit.

FIG. 7 shows a mechanism in which not only it is detected whether or not the option substrate is connected but also it is determined whether or not the option substrate is normally inserted and whether or not the operation is normal.

The power supply is turned on after attaching the option substrate and all the FPGA40 (only the single FPGA40 in FIG. 7 for purpose of a brief description) attached on the option substrate normally completes configuration. A clock CLK/synchronous signal is sent to all the FPGA40 from terminals Te' and Te and the like. The signal passes through the terminals Te' and Te, a signal returned to the connection processing circuit 37 is monitored, and it is determined whether or not the option substrate is normally attached.

FIG. 9B shows a display example of the menu screen when the normal attachment is detected (and the function in FIG. 6 is detected). FIG. 9A shows the menu screen when the option substrate is not attached. When the option substrate is not attached, referring to FIG. 9A, the function of the option substrate is displayed by a broken line. When the option substrate is normally attached, referring to FIG. 9B, the function of the option substrate is displayed by a solid line.

In place of FIG. 9A, referring to FIG. 9C, the function of the option substrate may not be displayed at all.

According to the second embodiment, as mentioned above, it is detected whether or not the option substrate is normally attached. If it is detected that the option substrate is normally detected, a more convenient device is realized by providing a function for displaying the menu content corresponding to the detected function of the option substrate.

Figure 10:
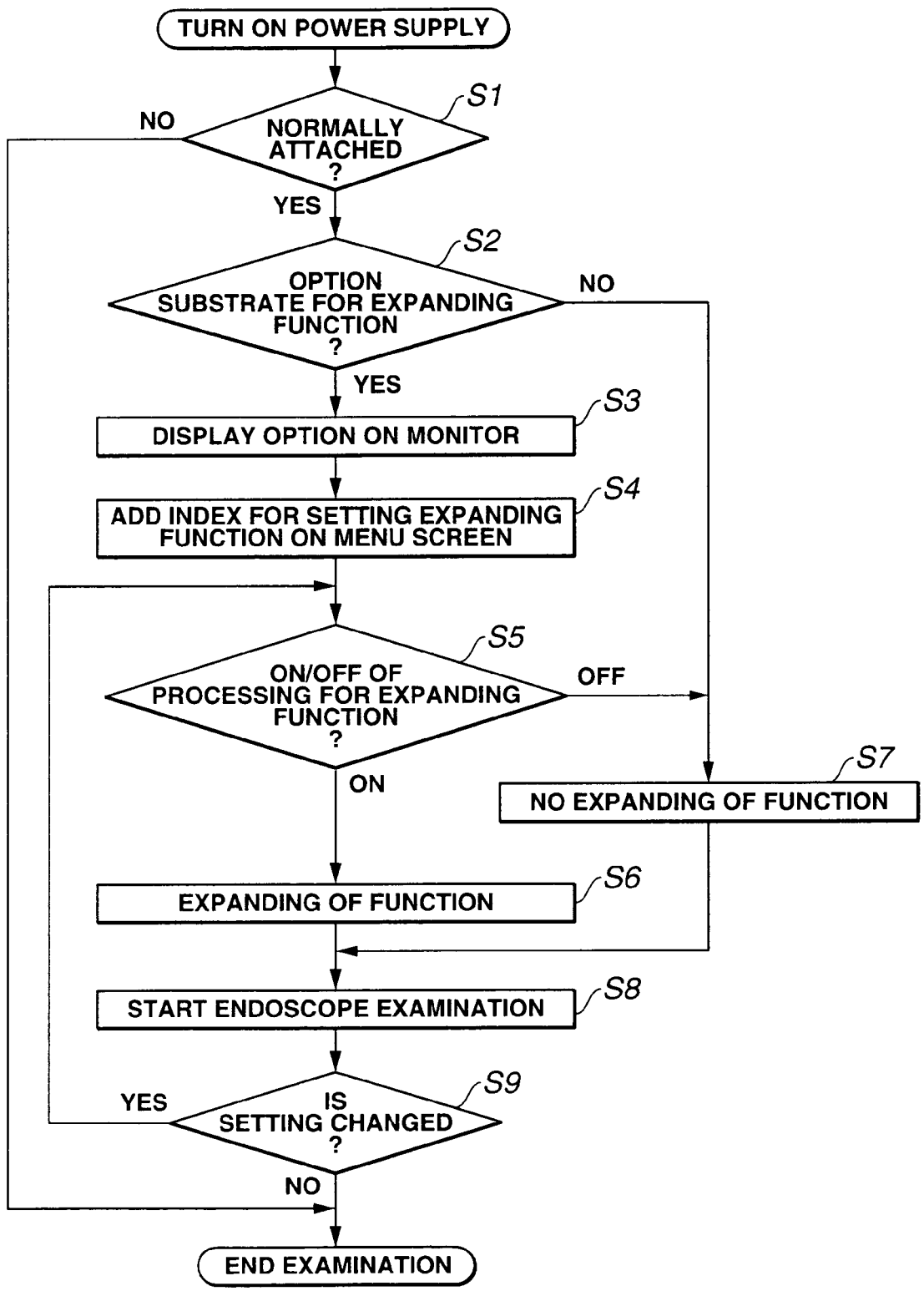
FIG. 10 is a flowchart for explaining the operation according to the second embodiment.

FIG. 10 shows a flowchart for explaining the operation according to the second embodiment. A power supply of the video processor 4 is turned on. Then, it is determined in step S1 whether or not the option substrate is normally attached. This determination is detected by the mechanism shown in FIG. 7. When the option substrate is not normally attached, the processing ends (the processing may end after displaying the error, before ending the processing).

When the option substrate is normally attached, in step S2, it is determined whether or not the option substrate is the option substrate for expanding the function. When it is determined that the option substrate is not the option substrate which expands the function, in step S7, processing without expanding the function is performed and the processing routine advances to processing for examination using the endoscope. On the other hand, when it is determined that the option substrate is the option substrate for expanding the function, in step S3, the "option" is displayed on the monitor 5 as shown in FIG. 8B and the processing routine advances to step S4.

In step S4, an index for setting the expansion of the function is added to the menu screen. Next, it is determined whether the processing of the index for the expansion of the function added in step S5 is ON/OFF. On the other hand, when the OFF operation is selected, the processing routine advances to step S7. When the ON operation is selected, the processing is set in a status in step S6 in which the function is expanded. The examination using the endoscope is started in step S8.

After starting the examination using the endoscope, in step S9, it is determined whether or not the setting is changed. When the setting is not changed, the examination using the endoscope ends. When the setting is changed, the processing routine returns to step S5 whereupon it is determined whether the processing of the index for the expansion of the function is ON/OFF.

According to the second embodiment, the connection of the option substrate is detected and it is displayed whether or not the option substrate is connected. The menu screen corresponding to the function which is selected by the attachment of the option substrate is displayed. The screen for setting the ON/OFF operation of the function is displayed. Accordingly, in addition to the advantages according to the first embodiment, the operability (convenience) can be improved.

Third Embodiment

Figure 11:
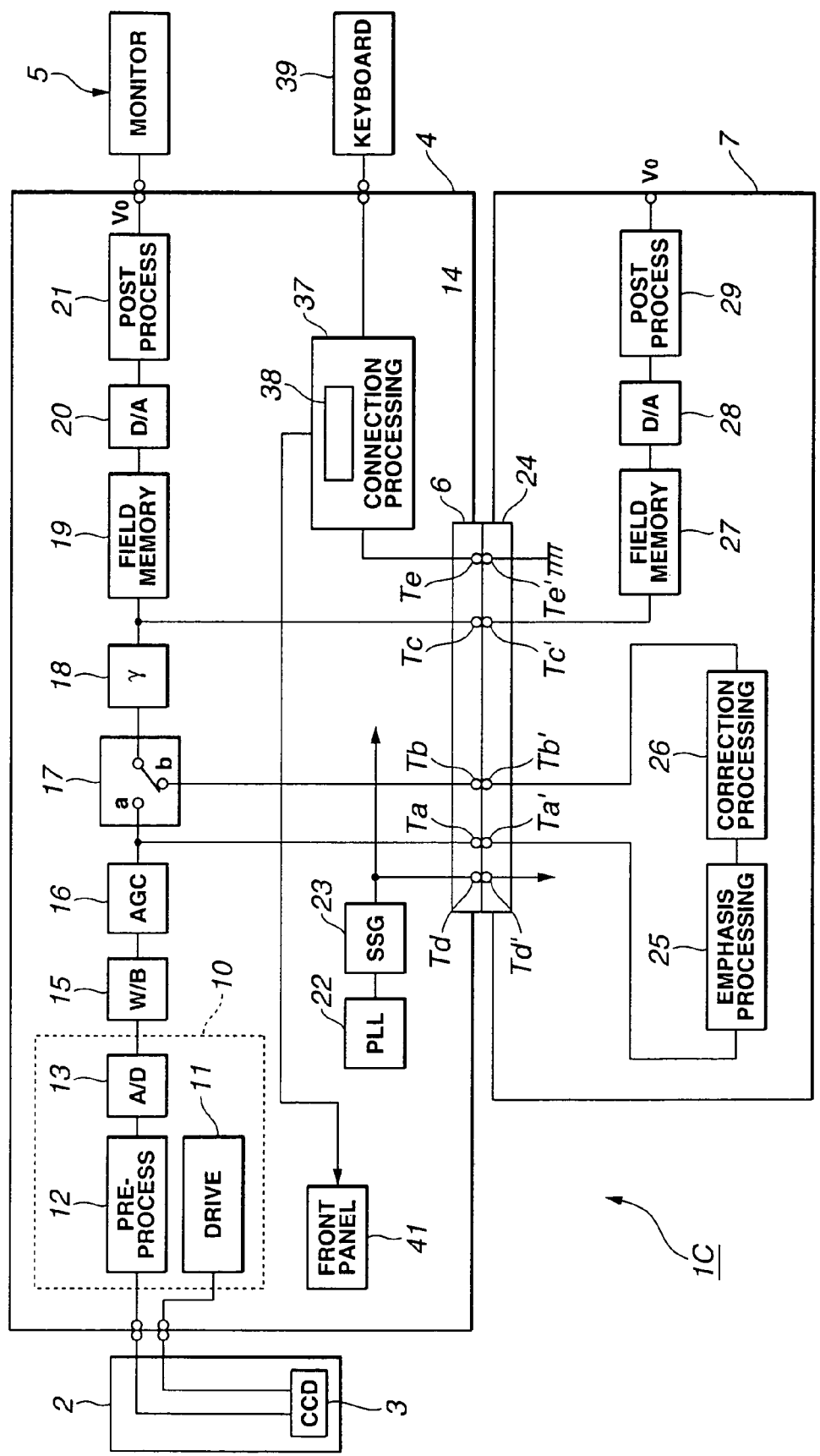
FIG. 11 is a block diagram showing the structure of an electronic endoscope apparatus according to a third embodiment of the present invention.

A third embodiment of the present invention will be described with reference to FIGS. 11, 12A and 12B. FIG. 11 shows an endoscope apparatus 1C according to the third embodiment. The endoscope apparatus 1C has the video processor 4 in the endoscope apparatus 1B in FIG. 5 in which an output of the connection processing circuit 37 for detecting the substrate connection is outputted to a front panel 41 of the video processor 4.

That is, according to the second embodiment, the result of detecting the connection is displayed on the monitor 5 shown in FIGS. 8A and 8B. However, according to the third embodiment, the result is displayed as shown in FIGS. 12A and 12B.

Figure 12A:
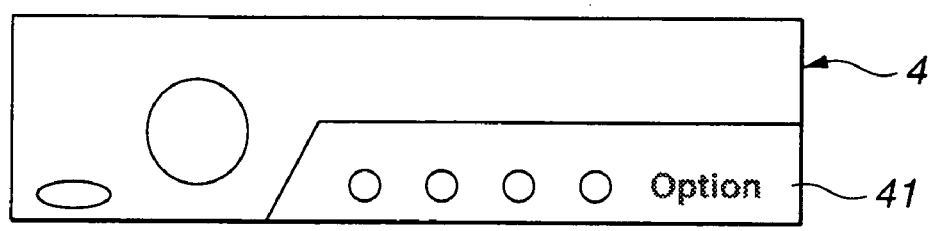
FIG. 12A is a diagram showing a display example of a front panel when the option substrate is not connected.

FIG. 12A shows a display example of the front panel when the option substrate is not connected. FIG. 12B shows a display example when the option substrate is connected.

Figure 12B:
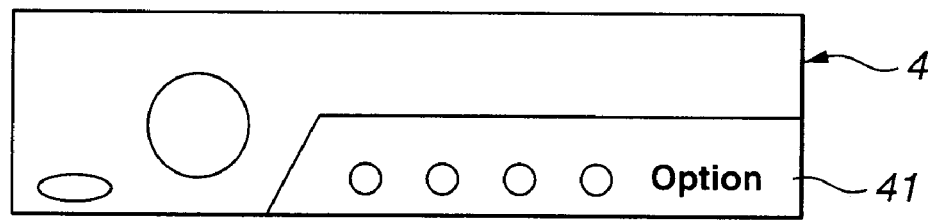
FIG. 12B is a diagram showing a display example of the front panel when the option substrate is connected.

FIG. 12B shows the display example when the result of detecting whether or not the option substrate is connected. Incidentally, although only the detection result of the substrate connection by the comparator C1 is displayed, a result for detecting another substrate function may be displayed.

The operation according to the third embodiment in which, in place of indicating the "option" on the monitor in step S3, the "option" is turned on the front panel and other operations are the same as those according to the second embodiment.

According to the third embodiment, the same advantages as those according to the second embodiment are obtained.

Fourth Embodiment

Figure 13:
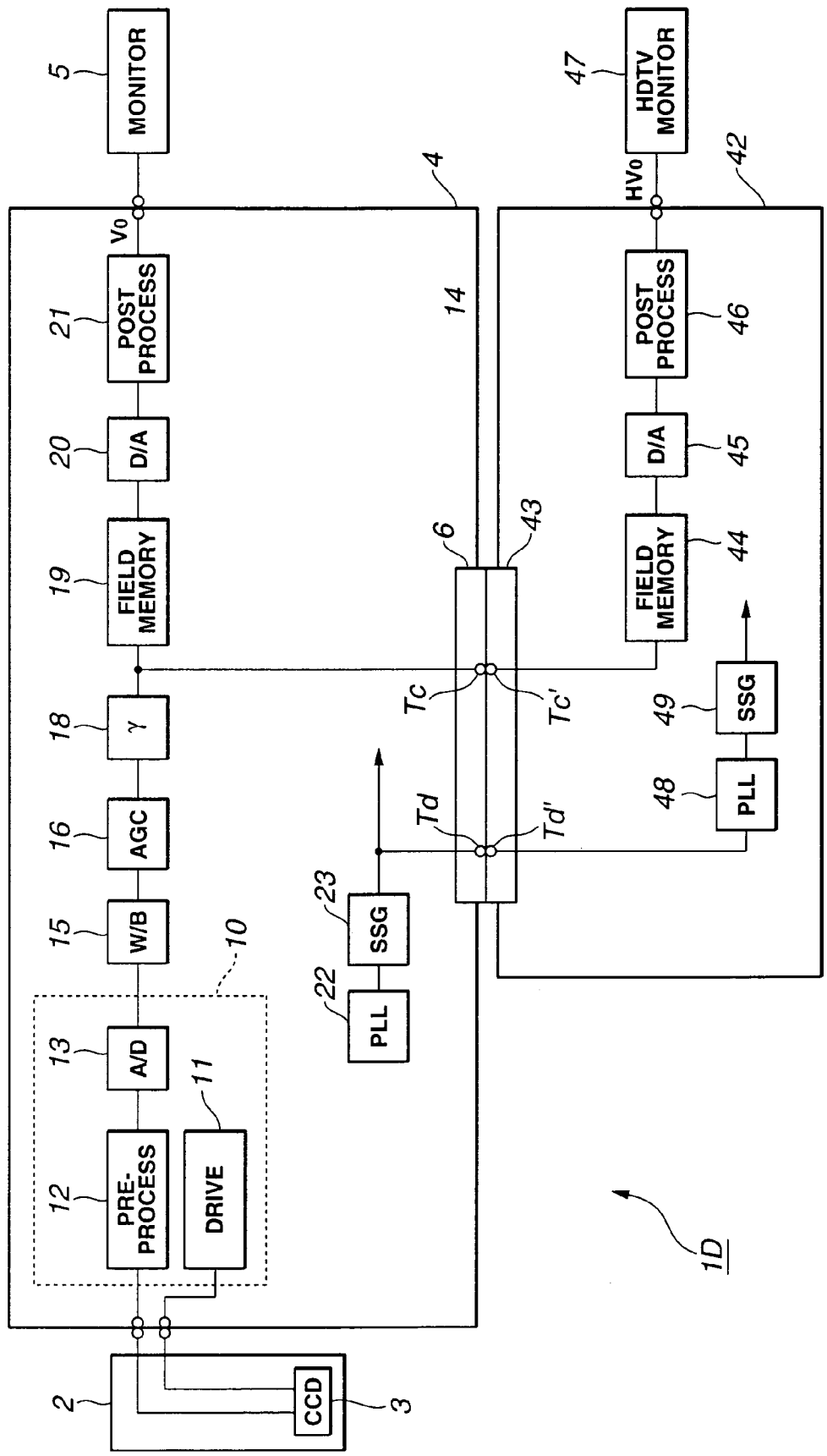
FIG. 13 is a block diagram showing the structure of an electronic endoscope apparatus according to a fourth embodiment of the present invention.

Next, according to a fourth embodiment of the present invention will be described with reference to FIGS. 13 and 14. FIG. 13 shows an endoscope apparatus 1D according to the fourth embodiment. The endoscope apparatus 1D is obtained by attaching an option substrate 42 shown in FIG. 14 to substantially the same video processing 4 as the endoscope apparatus 1A in FIG. 1.

Specifically, the video processor 4 shown in FIG. 13 is obtained by removing the selector 17 from the video processor 4 in FIG. 1. The option substrate 42 for generating an HDTV video signal can be attached to the video processor 4.

Figure 14:
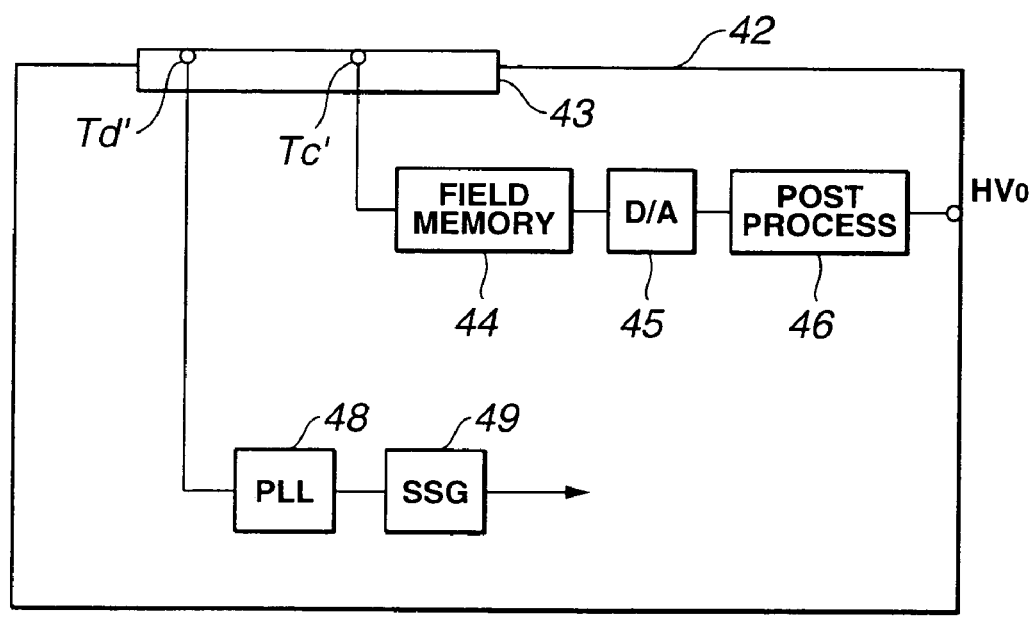
FIG. 14 is a block diagram showing the circuitry structure of an option substrate in FIG. 13.

Referring to FIG. 14, the option substrate 42 has a connector 43 connected to the connector 6. A field memory 44 is connected to the terminal Tc' of the connector 43 conductive to the terminal Tc of the connector 6. An output signal of the γ circuit 18 in the video processor 4 is temporarily stored and a signal read from the field memory 44 is converted into an analog signal by a D/A converting circuit 45. The field memory 44 has a storage capacity for displaying image information having one screen on an HDTV monitor 47 at the latter step.

The output signal from the D/A converting circuit 45 is converted into an HDTV video signal as another format video signal via a post-process circuit 46. After that, the converted signal is outputted from an HDTV output terminal HVo and an image with high quality can be displayed on the HDTV monitor 47 connected to the HDTV output terminal HVo.

A PLL circuit 48 is connected to the terminal Td' of the connector 43 conductive to the terminal Td of the connector 6. The output signal from the PLL circuit 48 is connected to an SSG circuit 49. A synchronous signal of the SSG circuit 49 is written to the field memory 44 of the option substrate 42 and is used for the control of the reading operation.

According to the fourth embodiment, the video processor 4 has a function for outputting the NTSC-format video signal. Further, the video processor 4 has a function for outputting a high-resolution format video signal by attaching the option substrate 42 for HDTV to the connector 6, thereby performing the examination using the endoscope.

According to the fourth embodiment, not only the normal video signal but also the HDTV video signal is generated, thereby performing the examination using the endoscope on the HDTV monitor 47.

Fifth Embodiment

Figure 15:
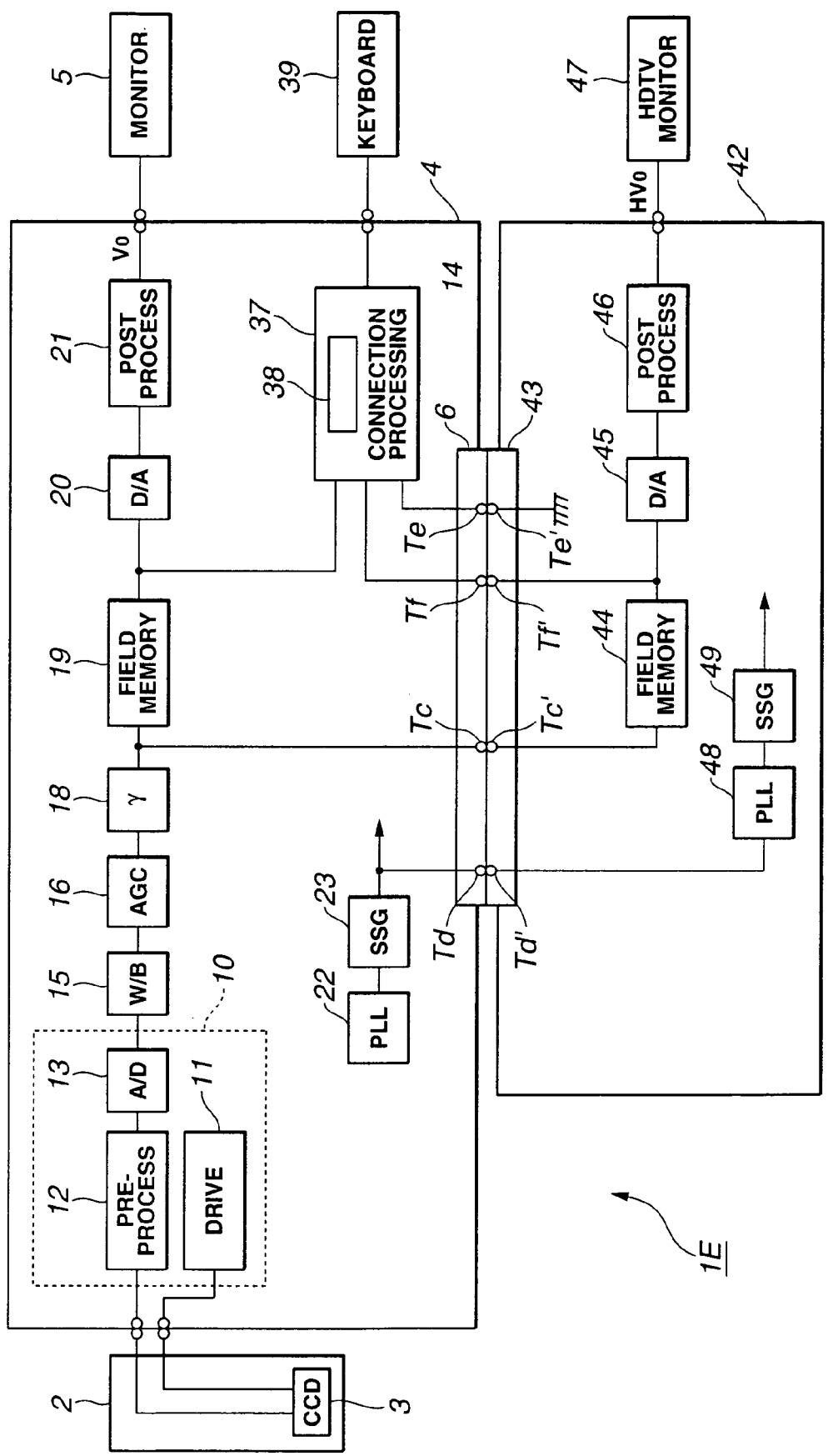
FIG. 15 is a block diagram showing the structure of an electronic endoscope apparatus according to a fifth embodiment of the present invention.

Next, a fifth embodiment of the present invention will be described with reference to FIGS. 15 to 19. FIG. 15 shows an endoscope apparatus 1E according to the fifth embodiment. The endoscope apparatus 1E comprises the connection processing circuit 37 for detecting whether or not the option substrate 42 is attached (connected) by detecting the level of the terminal Te of the connector 6 in the video processor 4 of the endoscope apparatus 1D in FIG. 13.

As described with reference to FIG. 5, the connection processing circuit 37 incorporates the character generating circuit 38. The generated character information is superimposed to the output data from the field memory 19 and is outputted to the D/A converting circuit 20 connected to the latter step. In the case of attaching the option substrate 42, the menu is displayed and the ON/OFF operation can be set from the key board 39 or the like.

Similarly to the case in FIG. 5, the terminal Te' of the connector 43 is connected to the ground. The connection processing circuit 37 detects the level of the terminal Te of the connector 6, thereby detecting whether or not the option substrate 42 is attached (connected).

Figure 16A:
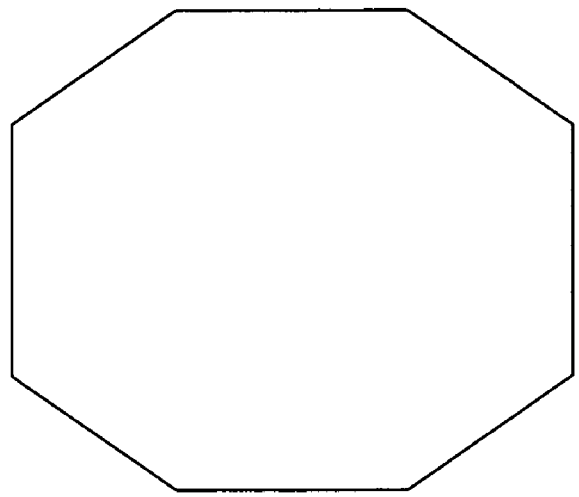
FIG. 16A is a diagram showing a display example of a HDTV monitor when an option substrate for HDTV is connected.
Figure 16B:
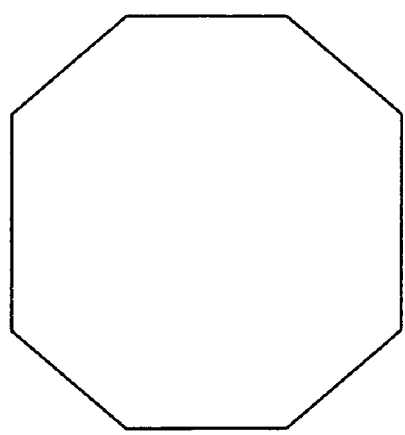
FIG. 16B is a diagram showing a display example of a normal monitor.

If it is detected that the option substrate 42 is attached, referring to FIG. 16A, an HDTV video image is displayed on a display screen of the HDTV monitor 47. Referring to FIG. 16B, a display example of the monitor 5 is shown so that it is understood that the NTSC video image is displayed.

Figure 17A:
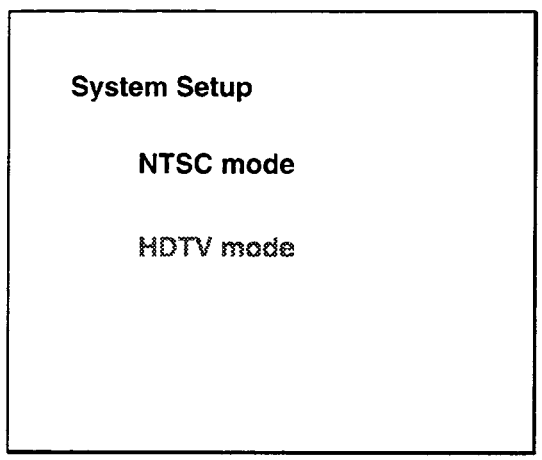
FIG. 17A is a diagram showing a display example of a menu screen when the option substrate is not connected.
Figure 17B:
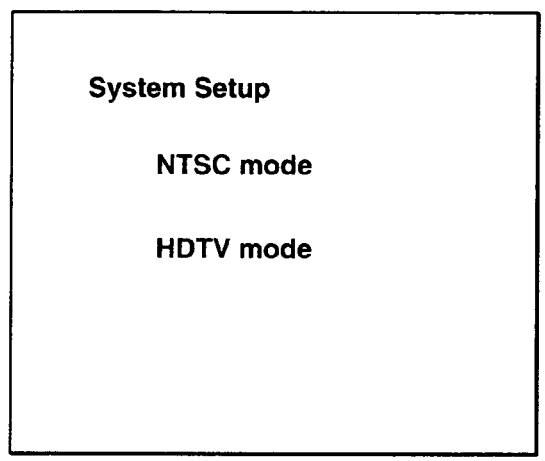
FIG. 17B is a diagram showing a display example of the menu screen when the option substrate is connected.

FIG. 17A shows a menu screen when the option substrate 42 is not attached, specifically, a system set-up screen. FIG. 17B shows a menu screen when the option substrate 42 is attached, specifically, the system set-up screen.

Figure 18A:
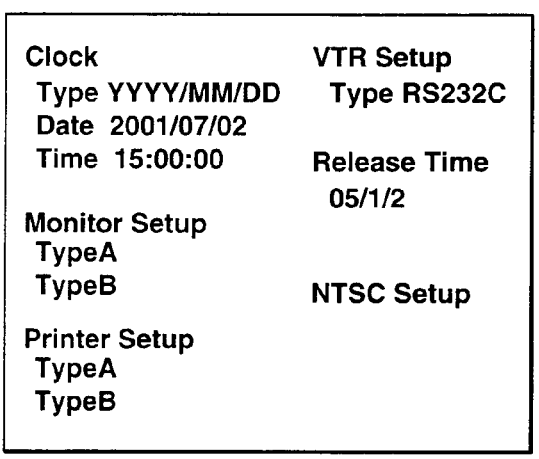
FIG. 18A is a diagram showing a display example of the menu screen on the normal monitor.
Figure 18B:
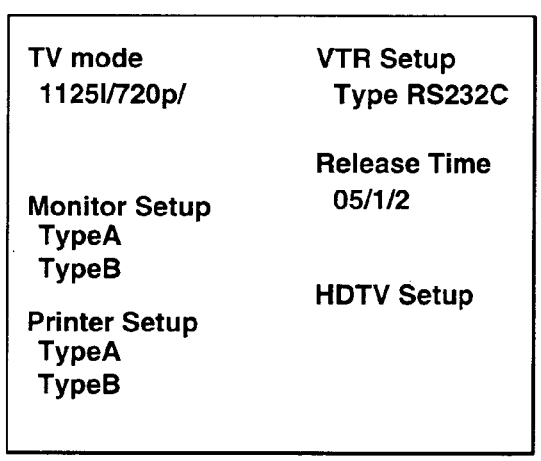
FIG. 18B is a diagram showing a display example of the menu screen on the HDTV monitor.

FIGS. 18A and 18B show a menu screen on the normal screen and a menu screen on the HDTV monitor screen, respectively.

FIG. 19 shows a flowchart of the operation according to the fifth embodiment. In the flowchart of FIG. 19, in place of the determination of the option substrate for expanding the function in the flowchart in FIG. 10, processing corresponding to the determination of the option substrate 42 for HDTV is performed.

Specifically speaking, the power supply of the video processor 4 is turned on. Then, first, in step S11, it is determined whether or not the option substrate is normally attached. The determination in step S11 is detected by the mechanism shown in FIG. 7. If the option substrate is not normally attached, the processing ends (the processing may end after displaying an error, before the end of processing).

If it is detected that the option substrate is normally attached, in step S12, it is determined whether or not the option substrate is the option substrate 42 for HDTV. If it is determined that the option substrate is not the option substrate for HDTV, the processing routine proceeds to step S17 whereupon only NTSC-system processing, that is, processing without expanding the function is performed. Then, the processing routine proceeds to step S18. On the other hand, if it is determined that the option substrate is the option substrate for HDTV, the processing routine proceeds to step S13 whereupon the HDTV image is displayed on the monitor 47 as shown in FIG. 16A. Then, the processing routine proceeds to step S14.

In step S14, an index for setting the HDTV monitor is added to the menu screen. In step S15, the added index for setting the HDTV monitor, that is, it is determined whether the HDTV video processing is ON/OFF. If it is determined that the processing is OFF, the processing routine proceeds to step S17. If it is determined that the processing is ON, the processing routine proceeds to step S16 whereupon the monitor is set to a state corresponding to the NTSC/HDTV systems and then, in step S18, the examination using the endoscope starts.

After starting the examination using the endoscope, in step S19, it is determined whether or not the setting is changed. If it is determined that the setting is not changed, the examination using the endoscope ends. If it is determined that the setting is changed, the processing routine returns to step S15 whereupon it is determined whether the HDTV video processing is ON/OFF.

According to the fifth embodiment, in addition to the advantages according to the fourth embodiment, the connection of the option substrate for HDTV is detected and it is displayed whether or not the option substrate is connected. The menu screen corresponding to the function added by the attachment of the option substrate can be displayed. The screen for setting the ON/OFF operation of the function can be displayed and thus the operability (convenience) can be improved.

Sixth Embodiment

Figure 20:
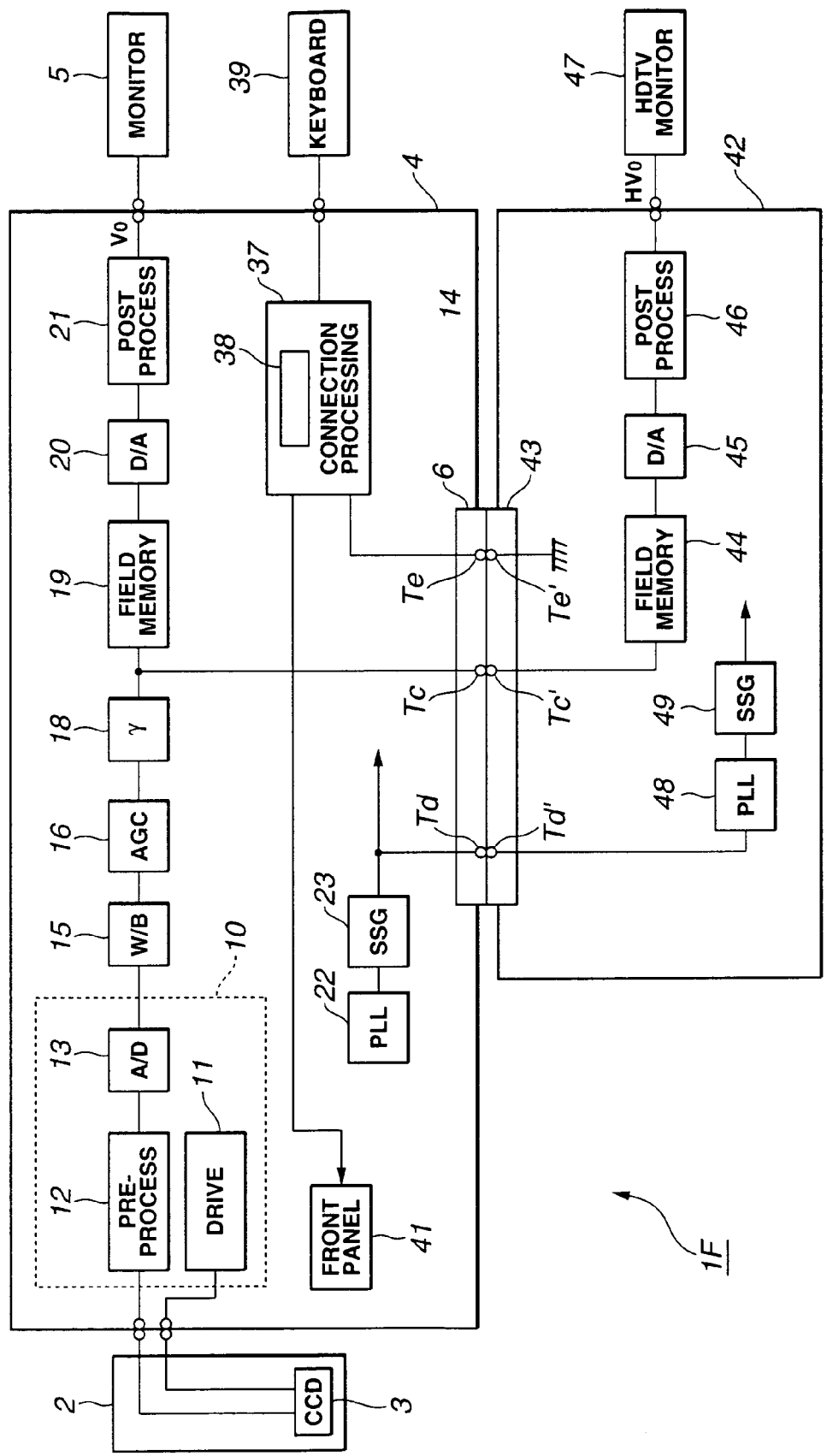
FIG. 20 is a block diagram showing the structure of an electronic endoscope apparatus according to a sixth embodiment of the present invention.

Next, a sixth embodiment of the present invention will be described with reference to FIGS. 20, 21A and 21B. FIG. 20 shows an endoscope apparatus 1F according to the sixth embodiment. The endoscope apparatus 1F has the structure in which information detected by the connection processing circuit 37 is displayed on the front panel 41 in the video processor 4 in the endoscope apparatus 1E of FIG. 15.

Figure 21A:
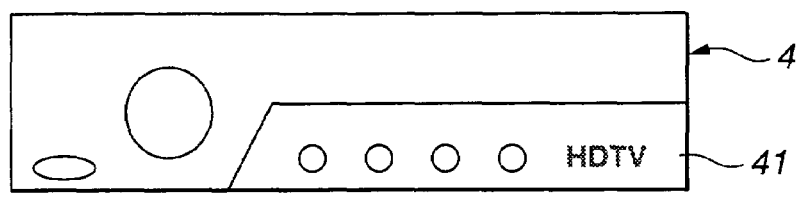
FIG. 21A is a diagram showing a display example of the front panel when the option substrate for HDTV is not connected.
Figure 21B:
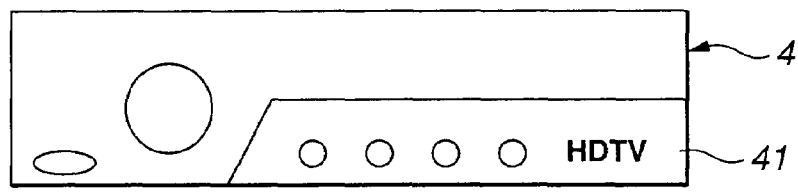
FIG. 21B is a diagram showing a display example of the front panel when the option substrate for HDTV is connected.

If the option substrate for HDTV is not connected, referring to FIG. 21A, an HTDV image is displayed as shown by a broken line. If the option substrate for HDTV is connected, referring to FIG. 21B, the HDTV image is displayed as shown by a solid line.

The operations and advantages according to the sixth embodiment are substantially the same as those according to the fifth embodiment.

Seventh Embodiment

Figure 23:
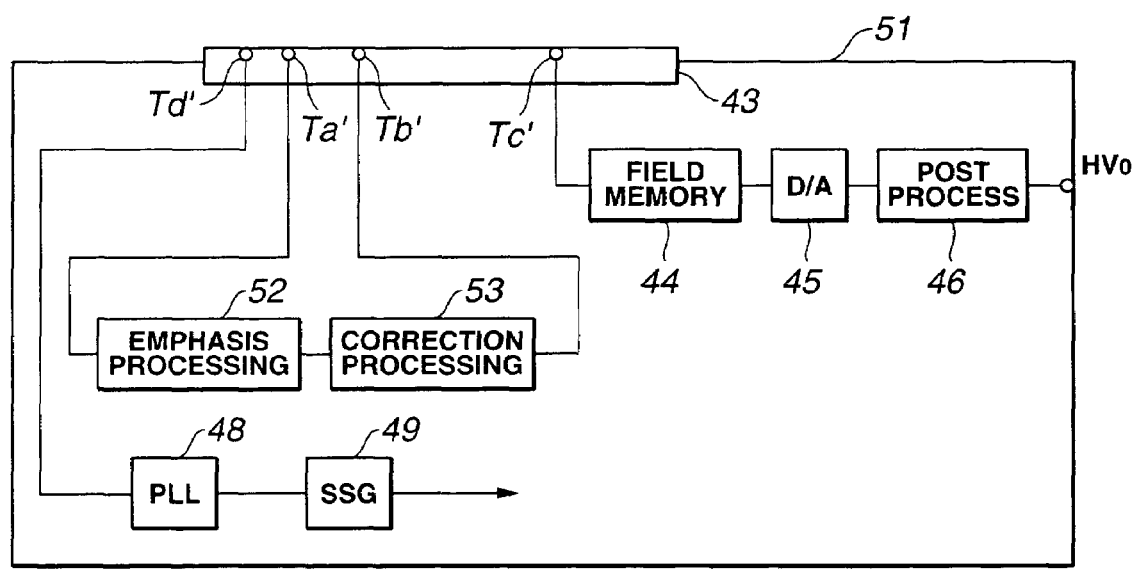
FIG. 23 is a block diagram showing the circuitry structure of the option structure for HDTV according to the seventh embodiment.
Figure 22:
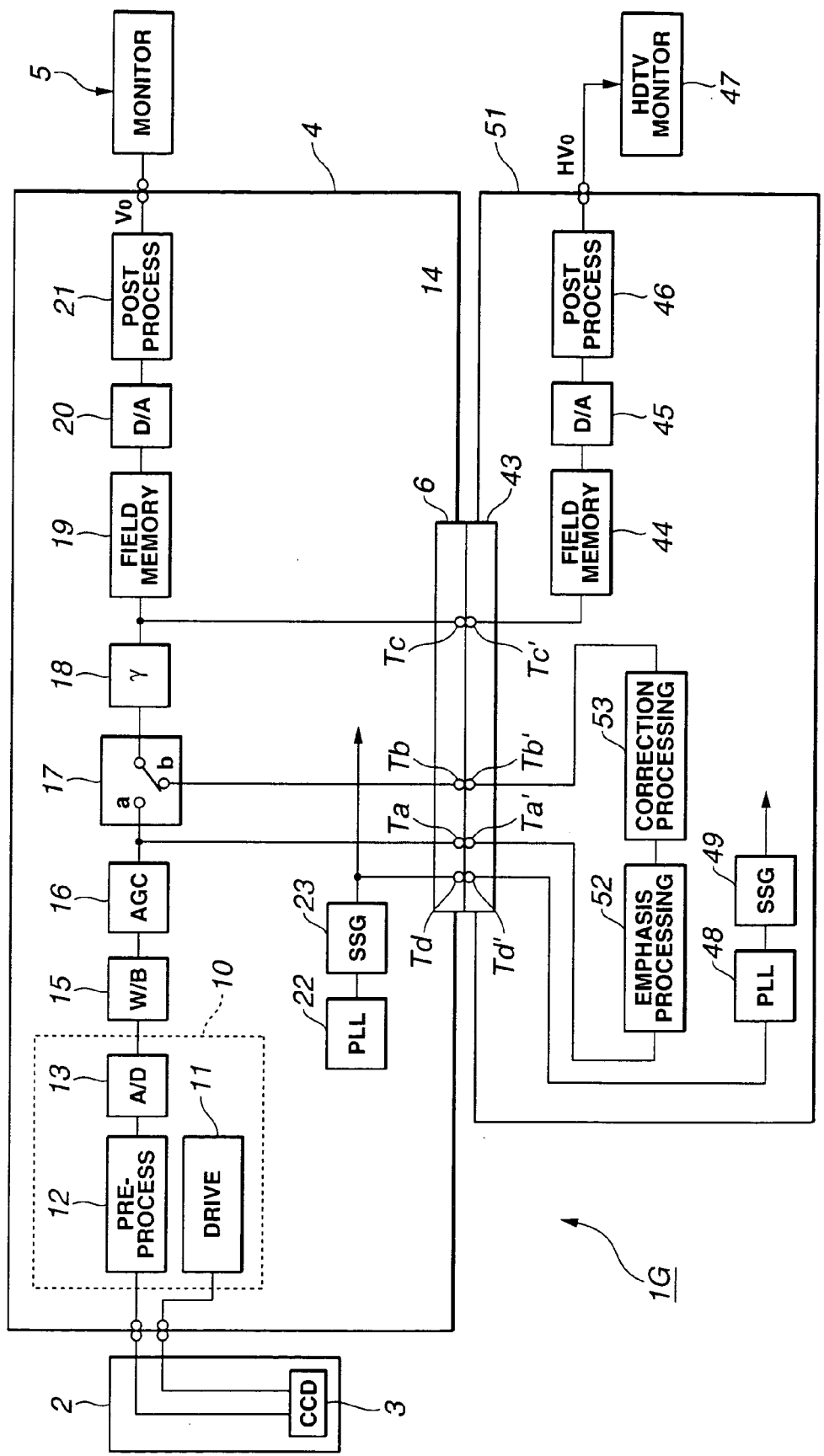
FIG. 22 is a block diagram showing the structure of an electronic endoscope apparatus according to a seventh embodiment of the present invention.
Figure 24:
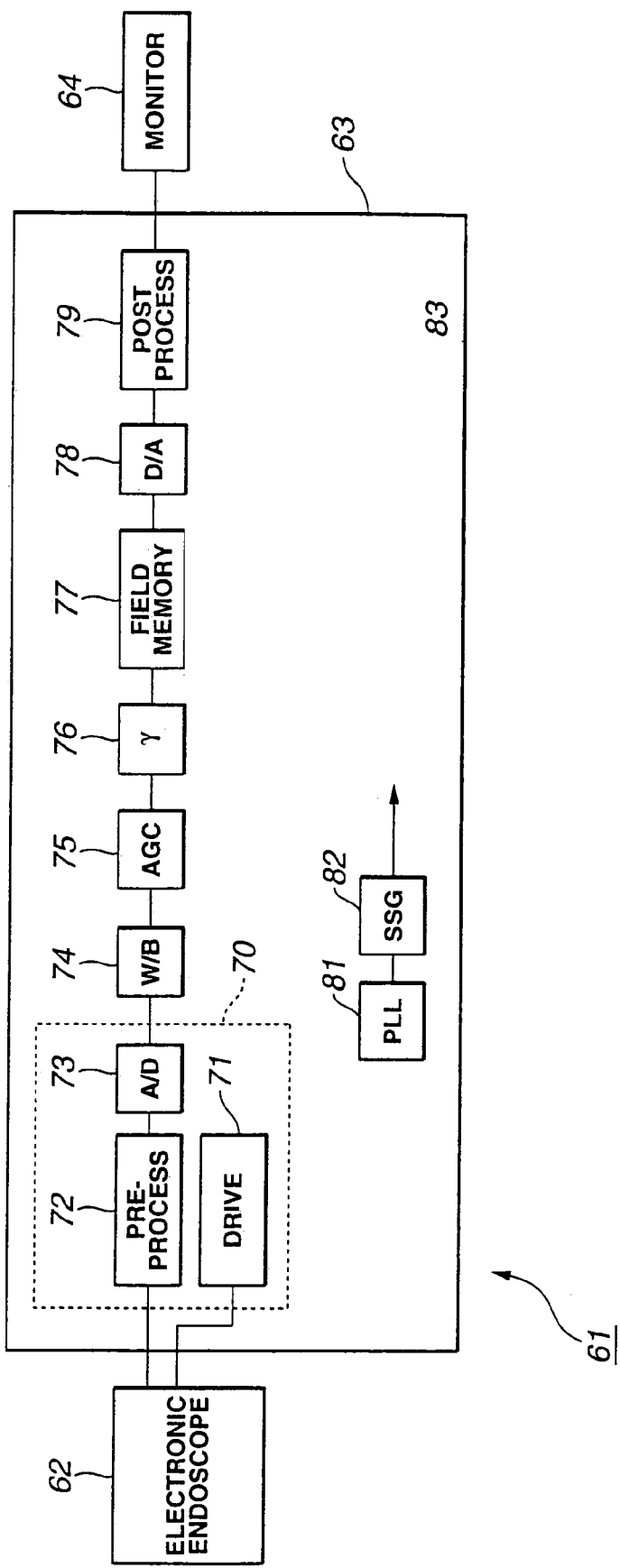
FIG. 24 is a block diagram showing the structure of a conventional electronic endoscope apparatus.

Next, a seventh embodiment of the present invention will be described with reference to FIGS. 22 and 23. FIG. 22 shows an endoscope apparatus 1G according to the seventh embodiment. The endoscope apparatus 1G has the structure in which the video processing 4 in the endoscope apparatus 1D in FIG. 13 comprises the selector 17 between the AGC circuit 16 and the γ circuit 18. The output of the AGC circuit 16 is outputted to the one contact a of the selector 17 and is applied to the terminal Ta of the connector 6. The signal is outputted to an option substrate 51 for HDTV which can be attached to the connector 6 as shown in FIG. 23.

The option substrate 51 for HDTV comprises an emphasis processing circuit 52 connected to the terminal Ta' conductive to the terminal Ta of the connector 6 on the option substrate 42 for HDTV in FIG. 14. After emphasis processing of the emphasis processing circuit 52, the signal is corrected by a correction processing circuit 53. The signal is returned to the selector 17 via the terminal Tb of the connector 6 conductive to the terminal Tb' of the connector 43. Other structure is the same as that shown in FIG. 13.

According to the seventh embodiment, in addition to the operations according to the fourth embodiment in FIG. 13, the emphasis processing is further performed and the processed image is displayed on the NTSC monitor 5 and the HDTV monitor 47.

In the above description, the single option substrate can be attached to the video processor 4. However, two or more option substrates may be attached.

The electronic endoscope having the image pick-up device such as the CCD 3 includes an optical endoscope having the image pick-up device.

Embodiments obtained by partly combining the above-mentioned embodiments or the like can belong to the present invention.

Further, the present invention is not limited to the above-mentioned embodiments but can be changed without departing the spirit of the present invention.

INDUSTRIAL APPLICABILITY

As mentioned above, according to the present invention, when the user desires a function for generating the basic video signal or an additional function, the attachment of the substrate or the detachment of the substrate enables wide users with low costs.

The invention claimed is:

1. An electronic endoscope apparatus comprising:
   an endoscope including an image pick-up device for converting a subject image into an image signal;
   a signal processing device for processing the image signal, the signal processing device including:
      a first signal processor that implements a signal process of the image signal and outputs to a first display device the processed image signal with a first television signal format having a first resolution; and
      a first connector adapted for connecting the signal processing device to a second signal processor;
   an option substrate having the second signal processor and a second connector for connecting the second signal processor to the signal processing device via the first connector, the second signal processor implements the signal process of the image signal and outputs to a second display device the processed image signal with a second television signal format having a second resolution that is higher than the first resolution; and
   a connection detector for detecting a connection of the second connector with the first connector and notifying a user of the connection, the connection detector including a connection detecting section that detects the connection, and a character information generating section that changes a displayed character information based on a signal from the connection detecting section.

2. The electronic endoscope apparatus as claimed in claim 1, wherein the character information generating section changes a displayed menu screen based on the signal from the connection detecting section.

3. An electronic endoscope apparatus comprising:
an endoscope including an image pick-up device for converting a subject image into an image signal;
a signal processing device for processing the image signal, the signal processing device including a first signal processor that implements a signal process of the image signal and outputs to a first display device the processed image signal with a first television signal format having a first resolution, and a connector;
a second signal processor detachably connected to the connector, the second signal processor implementing the signal process of the image signal and outputting to a second display device the processed image signal with a second television signal format having a second resolution that is higher than the first resolution; and
a connection detector for detecting a connection of the second signal processor with the connector and notifying a user of the connection, the connection detector including a connection detecting section that detects the connection, and a character information generating section that changes a displayed character information based on a signal from the connection detecting section.

4. The electronic endoscope apparatus as claimed in claim 3, wherein the character information generating section changes a displayed menu screen based on the signal from the connection detecting section.

5. An electronic endoscope apparatus comprising:
an endoscope including an image pick-up device for converting a subject image into an image signal;
a signal processing device including a first signal processor for processing the image signal, a second signal processor that implements a signal process of the processed image signal by the first signal processor in accordance with a first television signal format having a first resolution, a first output for outputting to a first display device the image signal processed by the second signal processor and a connector;
a signal processing section detachably connected to the connector, the signal processing section including a third signal processor that implements the signal process of the image signal processed by the first signal processor in accordance with a second television signal format having a second resolution that is higher than the first resolution, and a second output for outputting to a second display device the processed image signal by the third signal processor; and
a connection detector for detecting a connection of the connector with the signal processing section and notifying a user of the connection, the connection detector including a connection detecting section that detects the connection, a character information generating section that changes a displayed character information based on a signal from the connection detecting section.

6. The electronic endoscope apparatus as claimed in claim 5, wherein the signal processing section is provided with a substrate.

7. The electronic endoscope apparatus as claimed in claim 6, wherein the character information generating section changes a displayed menu screen based on the signal from the connection detecting section.

8. The electronic endoscope apparatus as claimed in claim 5, wherein the first signal processor includes an A/D converter for converting the image signal into a digital signal, and the signal processing section includes only a secondary circuit which is insulated from the A/D converter.

9. A signal processing apparatus comprising:
a first signal processor that implements a signal process of an image signal and outputs to a first display device the processed image signal with a first television signal format having a first resolution;
a second signal processor, which implements the signal process of the image signal and outputs to a second display device the processed image signal with a second television signal format having a second resolution that is higher than the first resolution;
a connector adapted for connecting to the second signal processor; and
a connection detector for detecting a connection of the second signal processor with the first signal processor and notifying a user of the connection, the connection detector including a connection detecting section that detects the connection, and a character information generating section that changes a displayed character information based on a signal from the connection detecting section.

10. The signal processing apparatus as claimed in claim 9, wherein the character information generating section changes a displayed menu screen based on the signal from the connection detecting section.

11. A signal processing apparatus comprising:
a first signal processor that implements a signal process of an image signal and outputs to a first display device the processed image signal with a first television signal format having a first resolution;
a connector;
a second signal processor detachably connected to the connector, the second signal processor implementing the signal process of the image signal and outputting to a second display device the processed image signal with a second television signal format having a second resolution that is higher than the first resolution; and
a connection detector for detecting a connection of the second signal processor with the first signal processor and notifying a user of the connection, the connection detector including a connection detecting section that detects the connection, and a character information generating section that changes a displayed character information based on a signal from the connection detecting section.

12. The signal processing apparatus as claimed in claim 11, wherein the character information generating section changes a displayed menu screen based on the signal from the connection detecting section.

13. A signal processing apparatus comprising:
a first signal processor for processing an image signal;
a second signal processor that implements a signal process of the processed image signal by the first signal processor in accordance with a first television signal format having a first resolution;
a first output for outputting to a first display device the image signal processed by the second signal processor;
a connector;
a signal processing section detachably connected to the connector, the signal processing section including a third signal processor that implements the signal process of the image signal processed by the first signal processor in accordance with a second television signal format having a second resolution that is higher than the first resolution, and a second output for outputting to a second display device the processed image signal by the third signal processor; and a connection detector for detecting a connection of the signal processing section with the connector and notifying a user of the connection, the connection detector including a connection detecting section that detects the connection, and a character information generating section that changes a displayed character information based on a signal from the connection detecting section.

14. The signal processing apparatus as claimed in claim 13, wherein the signal processing section is provided with a substrate.

15. The signal processing apparatus as claimed in claim 13, wherein the first signal processor includes an A/D converter for converting the image signal into a digital signal, and the signal processing section includes only a secondary circuit which is insulated from the A/D converter.

16. The signal processing apparatus as claimed in claim 13, wherein the character information generating section changes a displayed menu screen based on the signal from the connection detecting section.

17. An electronic endoscope apparatus comprising:
an endoscope including an image pick-up device for converting a subject image into an image signal;
a signal processing means for processing the image signal, the signal processing means including
  a first signal processing means for processing the image signal and outputting to a first display device the processed image signal with a first television signal format having a first resolution,
  a second signal processing means for processing the image signal and outputting to a second display device the processed image signal with a second television signal format having a second resolution that is higher than the first resolution, and
a connecting means to which the second signal processing means for is detachably connected; and
a connection detector for detecting a connection of the second signal processing means with the first signal processing means and notifying a user of the connection, the connection detector including a connection detecting section that detects the connection, and a character information generating section that changes a displayed character information based on a signal from the connection detecting section.

18. The electronic endoscope apparatus as claimed in claim 17, wherein the character information generating section changes a displayed menu screen based on the signal from the connection detecting section.

19. A signal processing apparatus comprising:
a first signal processing means for processing an image signal and outputting to a first display device the processed image signal with a first television signal format having a first resolution;
a second signal processing means for processing the image signal and outputting to a second display device the processed image signal with a second television signal format having a second resolution that is higher than the first resolution;
a connecting means to which the second signal processing means is detachably connected; and
a connection detector for detecting a connection of the second signal processing means with the first signal processing means and notifying a user of the connection, the connection detector including a connection detecting section that detects the connection, and a character information generating section that changes a displayed character information based on a signal from the connection detecting section.

20. The signal processing apparatus as claimed in claim 19, wherein the character information generating section changes a displayed menu screen based on the signal from the connection detecting section.

21. An electronic endoscope apparatus comprising:
an endoscope including an image pick-up device for converting a subject image into an image signal;
a signal processing device including a first signal processor for processing the image signal, a second signal processor that implements a signal process of the processed image signal by the first signal processor in accordance with a first television signal format having a first resolution, a first output for outputting to a first display device the image signal processed by the second signal processor and a connector; and
a signal processing section detachably connected to the connector, the signal processing section including a third signal processor that implements the signal process of the image signal processed by the first signal processor in accordance with a second television signal format having a second resolution that is higher than the first resolution, and a second output for outputting to a second display device the processed image signal by the third signal processor,
the first signal processor including an A/D converter for converting the image signal into a digital signal, and the signal processing section including only a secondary circuit which is insulated from the A/D converter.

22. An electronic endoscope apparatus comprising:
an endoscope including an image pick-up device for converting a subject image into an image signal;
a signal processing device including a first signal processor for processing the image signal, a second signal processor that implements a signal process of the processed image signal by the first signal processor in accordance with a first television signal format having a first resolution, a first output for outputting to a first display device the image signal processed by the second signal processor and a connector;
a signal processing section provided to a substrate detachably connected to the connector, the signal processing section including a third signal processor that implements the signal process of the image signal processed by the first signal processor in accordance with a second television signal format having a second resolution that is higher than the first resolution, and a second output for outputting to a second display device the processed image signal by the third signal processor; and
a connector detector for detecting a connection of the connector with the substrate and notifying a user of the connection, the connection detector including a connection detecting section that detects the connection, a character information generating section that chances a displayed character information based on a signal from the connection detecting section.

23. An electronic endoscope apparatus comprising:
an endoscope including an image pick-up device for converting a subject image into an image signal;
a signal processing device including a first signal processor for processing the image signal, a second signal processor that implements a signal process of the processed image signal by the first signal processor in accordance with a first television signal format having a first resolution, a first output for outputting to a first display device the image signal processed by the second signal processor and a connector;

a signal processing section provided to a substrate detachably connected to the connector, the signal processing section including a third signal processor that implements the signal process of the image signal processed by the first signal processor in accordance with a second television signal format having a second resolution that is higher than the first resolution, and a second output for outputting to a second display device the processed image signal by the third signal processor; and a connector detector for detecting a connection of the connector with the substrate and notifying a user of the connection, the connection detector including a connection detecting section that detects the connection, a character information generating section that changes a displayed character information based on a signal from the connection detecting section;

the character information generating section changing a displayed menu screen based on the signal from the connection detecting section.

24. A signal processing apparatus comprising:

a first signal processor for processing an image signal;

a second signal processor that implements a signal process of the processed image signal by the first signal processor in accordance with a first television signal format having a first resolution;

a first output for outputting to a first display device the image signal processed by the second signal processor;

a connector; and a signal processing section detachably connected to the connector, the signal processing section including a third signal processor that implements the signal process of the image signal processed by the first signal processor in accordance with a second television signal format having a second resolution that is higher than the first resolution, and a second output for outputting to a second display device the processed image signal by the third signal processor, the first signal processor including an A/D converter for converting the image signal into a digital signal, and the signal processing section including only a secondary circuit which is insulated from the A/D converter.

25. A signal processing apparatus comprising:

a first signal processor for processing an image signal;

a second signal processor that implements a signal process of the processed image signal by the first signal processor in accordance with a first television signal format having a first resolution;

a first output for outputting to a first display device the image signal processed by the second signal processor;

a connector;

a signal processing section provided to a substrate detachably connected to the connector, the signal processing section including a third signal processor that implements the signal process of the image signal processed by the first signal processor in accordance with a second television signal format having a second resolution that is higher than the first resolution, and a second output for outputting to a second display device the processed image signal by the third signal processor; and a connector detector for detecting a connection of the connector with the substrate and notifying a user of the connection, the connection detector including a connection detecting section that detects the connection, a character information generating section that changes a displayed character information based on a signal from the connection detecting section.

26. A signal processing apparatus comprising:

a first signal processor for processing an image signal;

a second signal processor that implements a signal process of the processed image signal by the first signal processor in accordance with a first television signal format having a first resolution, a first output for outputting to a first display device the image signal processed by the second signal processor;

a connector;

a signal processing section provided to a substrate detachably connected to the connector, the signal processing section including a third signal processor that implements the signal process of the image signal processed by the first signal processor in accordance with a second television signal format having a second resolution that is higher than the first resolution, and a second output for outputting to a second display device the processed image signal by the third signal processor; and a connector detector for detecting a connection of the connector with the substrate and notifying a user of the connection, the connection detector including a connection detecting section that detects the connection, a character information generating section that changes a displayed character information based on a signal from the connection detecting section, the character information generating section changing a displayed menu screen based on the signal from the connection detecting section.

* * * * *